(12) United States Patent
Kawaguchi et al.

(10) Patent No.: US 7,375,119 B2
(45) Date of Patent: May 20, 2008

(54) AMIDE TYPE CARBOXAMIDE DERIVATIVE

(75) Inventors: Takayuki Kawaguchi, Osaka (JP); Hidenori Akatsuka, Osaka (JP); Masamichi Morimoto, Osaka (JP); Tatsuya Watanabe, Osaka (JP); Toru Iijima, Osaka (JP); Jun Murakami, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 105 days.

(21) Appl. No.: 10/571,900

(22) PCT Filed: Sep. 24, 2004

(86) PCT No.: PCT/JP2004/013892

§ 371 (c)(1),
(2), (4) Date: Mar. 14, 2006

(87) PCT Pub. No.: WO2005/030706

PCT Pub. Date: Apr. 7, 2005

(65) Prior Publication Data

US 2006/0287329 A1    Dec. 21, 2006

(30) Foreign Application Priority Data

Sep. 26, 2003   (JP)   ............... 2003-334595

(51) Int. Cl.
A61K 31/44    (2006.01)
C07D 211/70   (2006.01)
C07D 413/00   (2006.01)

(52) U.S. Cl. .................. 514/340; 514/357; 546/337; 544/111

(58) Field of Classification Search ............. 546/337; 514/357, 340; 544/111
See application file for complete search history.

(56) References Cited

U.S. PATENT DOCUMENTS

| | | | |
|---|---|---|---|
| 6,380,221 | B1 | 4/2002 | Arnaiz et al. |
| 2003/0026521 | A1 | 2/2003 | Amin et al. |
| 2003/0069250 | A1 | 4/2003 | Zhu et al. |
| 2004/0029874 | A1 | 2/2004 | Beight et al. |

FOREIGN PATENT DOCUMENTS

| | | |
|---|---|---|
| WO | WO-99/00121 A1 | 1/1999 |
| WO | WO-99/42439 | 8/1999 |
| WO | WO-00/39118 A1 | 7/2000 |
| WO | WO-01/19788 A2 | 3/2001 |
| WO | WO-02/12189 A1 | 2/2002 |
| WO | WO-02/019145 A1 | 10/2002 |
| WO | WO-02/079145 A1 | 10/2002 |
| WO | WO-03/082847 A1 | 10/2003 |
| WO | WO-04/063202 A1 | 7/2004 |
| WO | WO-2004/063202 A1 | 7/2004 |

OTHER PUBLICATIONS

Ying, K. Yee et al., Journal of Medicinal Chemistry, 2000, vol. 43, NO. 5, pp. 873-882.

Freedman, "Oral Anticoagulants: Pharmacodynamics, Clinical Indications and Adverse Effects", Journal of Clinical Pharmacology, vol. 32, pp. 196-209, 1992.

Hirsh, "Oral Anticoagulant Drugs", The New England Journal of Medicine, vol. 324, No. 26, pp. 1865-1875, 1991.

Sixma, et al., "The Ideal Anti-Thrombotic Drug", Thrombosis Research, Erratum, vol. 68, pp. 507-512, 1992.

(Continued)

*Primary Examiner*—Janet L. Andres
*Assistant Examiner*—Binta Robinson
(74) *Attorney, Agent, or Firm*—Birch, Stewart, Kolasch & Birch, LLP

(57) ABSTRACT

The present invention provides an amide-type carboxamide derivative of the formula [1]:

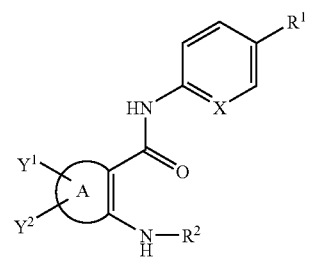

[1]

wherein X is a group of the formula: —N= or the formula: —CH=; $R^1$ is a halogen atom, a lower alkyl group, and the like; $R^2$ is a group of the formula:

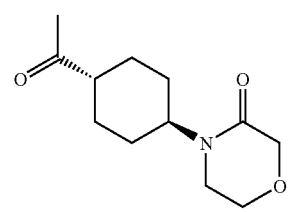

and the like; $Y^1$ and $Y^2$ are the same or different and each is a group selected from a halogen atom, a lower alkyl group, a lower alkoxy group, and the like; Ring A is phenyl group, and the like, or a pharmaceutically acceptable salt thereof, which is useful as an inhibitor of FXa.

7 Claims, No Drawings

OTHER PUBLICATIONS

Matsuo, "t-PA and Pro-UK", Gakusaikikaku, pp. 5-40, 1986.

Kaiser, et al., "Pharmacological Characterization of a New Highly Effective Synthetic Thrombin Inhibitor", Biomedica Biochim Acta, vol. 44, 7/8, pp. 1201-1210, 1985.

Tidwell, et al., "Strategies for Anticoagulation with Synthetic Protease Inhibitors, Xa Inhibitors Versus Thrombin Inhibitors", Thrombosis Research, vol. 19, pp. 339-349, 1980.

Harwalkar, et al., "Synthesis and Reactions of 2-Substituted-4H-Benzofuro[3,2-d]-m-Oxazin-4-Ones", Indian Journal of Heterocyclic Chemistry, vol. 3, pp. 247-252, 1994.

Viti, et al., "Synthesis of New Arylbenzofurodiazepin-6-ones", Journal of Heterocyclic Chemistry, 27(5), pp. 1369-1375, 1990.

Sogorinsho 41, pp. 2913-2918, 1992 (short English summary).

Ying, K. Yee et al., Journal of Medicinal Chemistry, 2000, vol. 43, No. 5, pp. 873-882.

AMIDE TYPE CARBOXAMIDE DERIVATIVE

TECHNICAL FIELD

The present invention relates to amide-type carboxamide derivatives useful as a medicament, particularly as an inhibitor of activated blood coagulation factor X (hereinafter, referred to as "FXa"), or a pharmaceutically acceptable salt thereof.

BACKGROUND ART

In late years, as the westernization of living habit and the aging of populations, thromboembolic diseases such as myocardial infarction, cerebral infarction and peripheral arterial thrombosis increase year by year, and social importance of treatment thereof has risen more and more.

Among therapies of thromboembolic diseases, anticoagulant therapy, as well as fibrinolytic therapy and antiplatelet therapy, takes part in medical therapy for treatment and prevention of thrombosis (Sogorinsho 41: 2141-2145, 1989). In particular, the safety sustainable to chronic administration and the reliable and appropriate expression of anticoagulant activity are essential in the prevention of thrombosis. A coumarin derivative, especially warfarin potassium, has often been used all over the world as an anticoagulant available orally. However, owing to the characteristics arisen from the mechanism of action, it requires long time until the drug efficacy manifests and has very long half-life in blood, although the concentration range for expression of drug efficacy is relatively narrow, and also shows significant differences in the effective dose among individuals. For these reasons, the anticoagulant ability can hardly be controlled (Journal of Clinical Pharmacology, 1992, vol. 32, pp. 196-209; NEW ENGLAND JOURNAL OF MEDICINE, 1991, vol. 324, no. 26, pp. 1865-1875). In addition, there may be adverse drug reactions such as risk of bleeding, nausea, vomiting, diarrhea, depilation, and the like, and therefore the clinical application thereof is very difficult and the development of anticoagulants that are useful and easy to handle has been demanded.

In addition, enhancement of blood clotting ability is one of significant causative factors of unstable angina, cerebral infarction, cerebral embolism, myocardial infarction, pulmonary infarction, pulmonary embolism, Buerger's disease, deep vein thrombosis, disseminated intravascular coagulation, thrombogenesis after artificial heart valve displacement, reocclusion after blood circulation reconstruction and thrombogenesis during extracorporeal circulation, and the like. Therefore, a distinguished anticoagulant that shows good dose response and lower risk of hemorrhage with few side-effects, and can exert sufficient effects upon oral administration has been desired (Thrombosis Research, 1992, vol. 68, pp. 507-512).

Thrombin participates not only in the conversion of fibrinogen to fibrin, which is the final stage of the coagulation cascade, but also deeply in the activation and aggregation of blood platelets (Matsuo, O., "t-PA and Pro-UK", Gakusaikikaku, 1986, pp. 5-40), and an inhibitor thereof has long been the center of the research in anticoagulants as a target of development of new drugs. However, a thrombin inhibitor shows low bioavailability upon oral administration and also has drawbacks in regard to safety such as bleeding tendency as one of side effects (Biomedica Biochimica Acta, 1985, Vol. 44, p. 1201-1210).

FXa is a key enzyme located in the position of the common pathway of both extrinsic and intrinsic coagulation cascade reactions. FXa is located upstream from thrombin in the coagulation cascade. Therefore, the inhibition of FXa is possibly more effective and specific in the inhibition of coagulation system compared to the inhibition of thrombin (Thrombosis Research, 1980, Vol. 19, pp. 339-349).

Thus a substance which inhibits FXa and shows distinguished enzyme selectivity and high bioavailability is expected to undergo control of its anticoagulant activity for a long period of time and can express superior therapeutic effect upon oral administration compared to the existing anticoagulants. Accordingly, the development of a novel inhibitor of FXa that can be administered orally has been earnestly demanded.

Examples of known compounds having inhibitory effect on FXa include thiobenzamide compounds that are useful in prevention or treatment of thrombosis (WO99/42439).

The following benzofuran compounds have also been known (Indian Journal of Hetero Cyclic Chemistry, 1994, Vol. 3, pp. 3247-3252), but said literature does not mention about the inhibitory effect of the compounds on FXa.

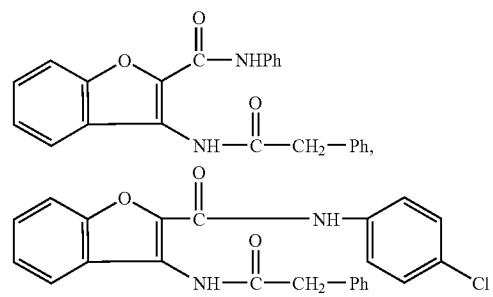

Condensed bicyclic amide compounds of the formula:

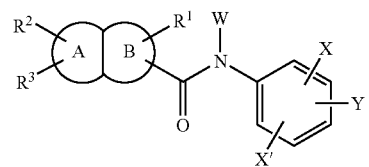

which has an activity of suppressing the growth of activated lymphocytes and are useful as a drug for preventing or treating autoimmune diseases are also known (WO02/12189). The WO02/12189 does not mention about the inhibitory effect on FXa either. In the pamphlet, compounds having a condensed ring of pyridine and furan to which ring an amide and a carbamoyl groups are di-substituted are disclosed; however, said compounds all have a benzene ring on the nitrogen atom of the carbamoyl group, said benzene ring being substituted by X and Y simultaneously.

DISCLOSURE OF INVENTION

The present invention provides a novel amide-type carboxamide derivative having excellent inhibitory effect on FXa, or pharmaceutically acceptable salts thereof.

The present inventors have intensively studied and have found that an amide-type carboxamide derivative of the formula below has excellent inhibitory effect on FXa and have accomplished the present invention.

That is, the present invention is as follows:

1. An amide-type carboxamide derivative of the formula [1]:

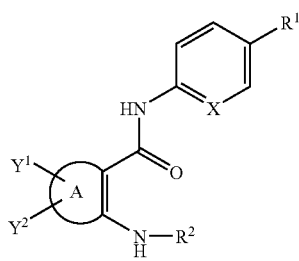

[1]

wherein X is a group of the formula: —N═ or the formula: —CH═;
$Y^1$ and $Y^2$ are the same or different and each is a group selected from a hydrogen atom, a halogen atom, a lower alkyl group, a lower alkoxy group, a lower alkyl group substituted by halogen atom, a lower alkoxycarbonyl group, a carboxyl group, a lower alkylcarbamoyl group and a phenyl group;
$R^1$ is a hydrogen atom, a halogen atom, a lower alkyl group or a lower alkoxy group;
$R^2$ is a group of the formula: —CO—$R^{21}$—$R^{22}$;
$R^{21}$ is a lower alkylene group or a cycloalkanediyl group; and
$R^{22}$ is a group of the formula:

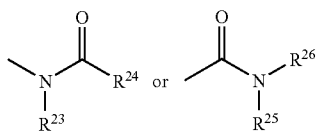

wherein $R^{23}$ and $R^{24}$ are the same or different and each is a lower alkyl group or an amino-lower alkyl group optionally substituted by a lower alkyl group; or combine together at the ends to form an optionally substituted nitrogen-containing saturated heterocyclic group along with the adjacent group: —N—C(═O)—; $R^{25}$ and $R^{26}$ are the same or different and each is a lower alkyl group or an amino-lower alkyl group optionally substituted by a lower alkyl group; or combine together at the ends to form an optionally substituted nitrogen-containing saturated heterocyclic group along with the adjacent nitrogen atom; and Ring A is an aromatic hydrocarbon, a monocyclic heteroaromatic ring or a condensed thiophene ring, or a pharmaceutically acceptable salt thereof.

2. The compound according to 1 above, wherein Ring A is benzene, naphthalene, pyridine, furan, thiophene, pyrazole, benzothiophene or thienopyridine.

3. The compound according to 2 above, wherein $R^2$ is

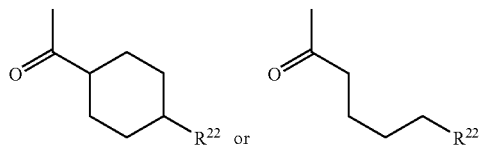

$R^{22}$ is a group of the formula:

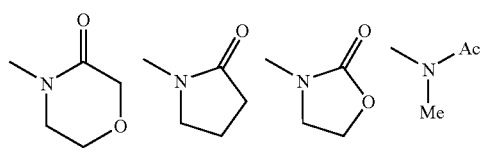

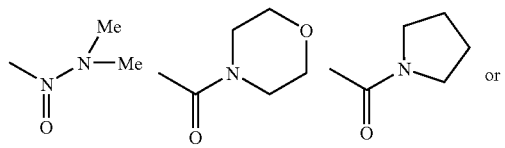

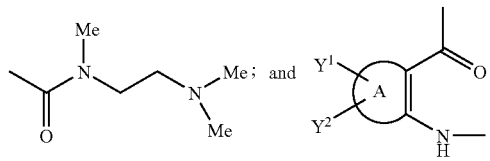

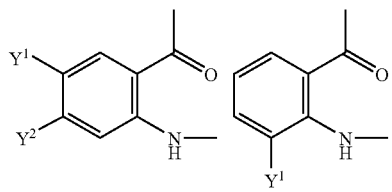

is a group of the formula:

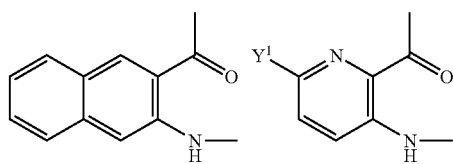

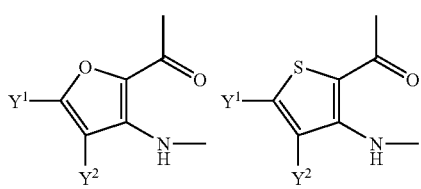
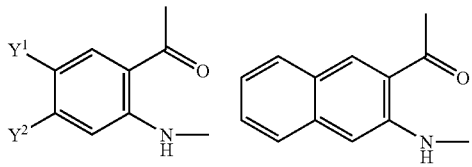

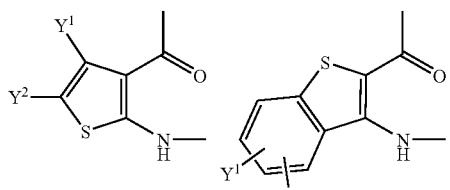

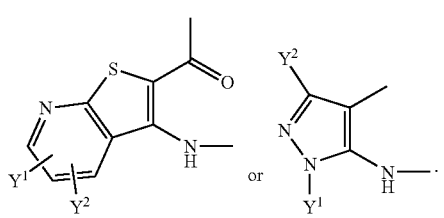
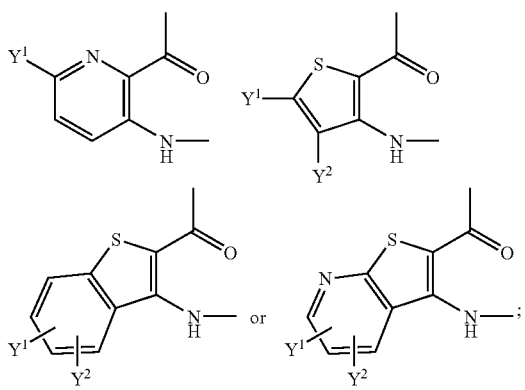

and

Y¹ and Y² are the same or different and each is a group selected from a hydrogen atom, a halogen atom, a lower alkyl group, a lower alkoxy group and a carboxyl group.

5. The compound according to 4 above, wherein

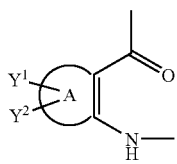

is a group of the formula:

4. The compound according to 2 above, wherein R¹ is a halogen atom or a lower alkyl group;

R² is a group of the formula:

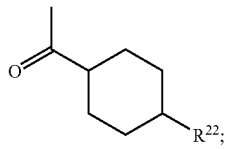

R²² is a group of the formula:

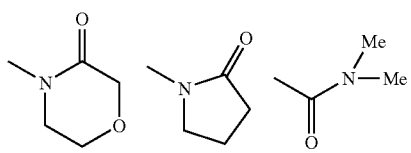

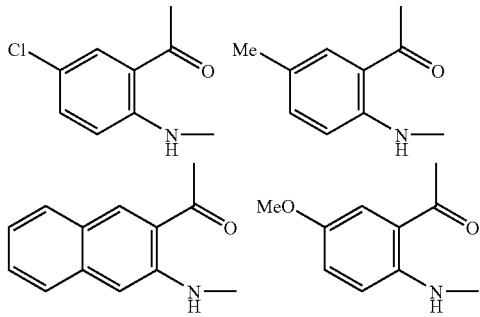

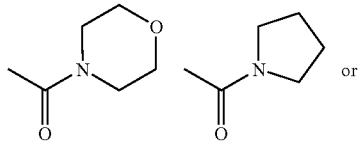

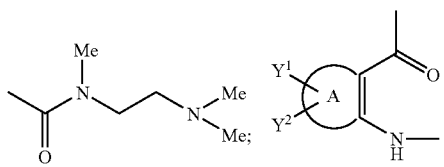

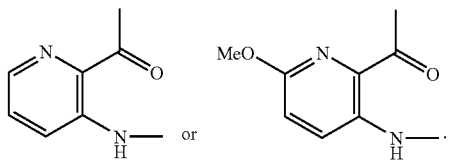

is a group of the formula:

6. A pharmaceutical composition, which comprises as an active ingredient a compound according to any one of 1 to 5 above, or a pharmaceutically acceptable salt thereof.

7. A method for treatment of thrombosis, which comprises administering an effective amount of a compound according to any one of 1 to 5 above, or a pharmaceutically acceptable salt thereof, to a patient in need thereof 8. Use of a compound according to any one of 1 to 5 above, or a pharmaceutically acceptable salt thereof in treatment of patients suffering from thrombosis.

BEST MODE FOR CARRYING OUT THE INVENTION

The compound [1] of the present invention will be hereinafter described in detail.

The term "lower" used in the definition of the formulas herein described means unless otherwise noted a straight- or branched-carbon chain having 1 to 6 carbon atoms.

Thus, examples of "lower alkyl group" include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, and the like. Among them, alkyl groups having 1 to 4 carbon atoms, for example, methyl, ethyl, propyl, isopropyl, butyl, isobutyl, sec-butyl and tert-butyl are commonly used.

The term "lower alkoxy group" means a substituent wherein an oxygen atom is bound to the above-mentioned alkyl group. Among them, alkoxy groups having 1 to 4 carbon atoms, for example, and methoxy, ethoxy, propoxy, isopropoxy, butoxy, isobutoxy, sec-butoxy and tert-butoxy groups are commonly used.

Examples of "lower alkylene group" include a straight- or branched-chain alkylene group having 1 to 6 carbon atoms, specifically, methylene, ethylene, trimethylene, tetramethylene, pentamethylene, hexamethylene, and the like. Among them, an alkylene group having 1 to 5 carbon atoms is preferred.

Examples of "cycloalkanediyl group" include 3- to 7-membered cycloalkanediyl group such as 1,4-cyclohexanediyl group.

Examples of "aromatic hydrocarbon group" include benzene, naphthalene, anthracene, phenanthrene, and the like, and also condensed rings. Among them benzene and naphthalene are commonly used.

The "monocyclic heteroaromatic ring" means a monocyclic heteroaromatic ring containing 1 to 4 hetero atoms selected independently from a group consisting of nitrogen atom, oxygen atom and sulfur atom. Among them, 5- to 7-membered heterocyclic groups are commonly used and specific examples include pyridine, furan, thiophene, pyrazole, pyrrole, oxazole, isoxazole, thiazole, isothiazole, imidazole, pyridazine, pyrimidine or pyrazine.

The "condensed thiophene ring" means a condensed ring wherein a thiophene ring and a cyclic compound are condensed, for example, benzothiophene and thienopyridine.

The "nitrogen-containing saturated heterocyclic group" means a saturated ring containing 1 to 4 hetero atoms, which ring may contain, in addition to nitrogen atom, oxygen atom and/or sulfur atom. Among them, 4 to 14-membered saturated heterocyclic groups containing, as hetero atom, only nitrogen atom or those containing both nitrogen atom and oxygen atom, including condensed rings, are commonly used. Specific examples include imidazolidinyl, pyrazolidinyl, piperidyl, piperazinyl, morpholinyl, thiomorpholinyl, homopiperazinyl, homopiperidyl, pyrrolidinyl, oxazolidinyl, and the like.

Examples of "halogen atom" include fluorine, chlorine, bromine or iodine atom. Above all, fluorine, chlorine or bromine atom is preferred.

The pharmaceutically acceptable salt of the compound [1] includes a salt with an inorganic acid such as hydrochloric acid, hydrobromic acid, hydroiodic acid, sulfuric acid, nitric acid, phosphoric acid, and the like; a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, and the like; salt with an acidic amino acid such as aspartic acid, glutamic acid, and the like; salt with a metal such as sodium, potassium, magnesium, calcium, aluminium, and the like; salt with an organic base such as methylamine, ethylamine, ethanolamine, and the like; or a salt with a basic amino acid such as lysine, ornithine, and the like.

The compound [1] of the present invention can be in the form of quaternary ammonium salt and such a quaternary ammonium salt falls within the scope of the present compound [1].

Further, the compound [1] of the present invention includes an intramolecular salt, hydrate, solvate or crystalline polymorphism, and the like.

Besides, when the compound [1] has an asymmetric carbon atom(s), it can exist as an optical isomer, and the present invention encompass those isomers and a mixture thereof. Further, when the compound [1] has a double bond and/or a ring to which a cycloalkanediyl group having two or more substituents is attached, it may exist in the form of cis or trans, and the present invention encompass those isomers and a mixture thereof.

Additionally, the compound [1] of the present invention encompasses a prodrug of a compound as mentioned above. Examples of a prodrug include those prepared by protecting a functional group such as an amino or carboxy group of a compound [1] above with a conventional protecting group.

The compound of the present invention may be prepared by the following processes.

[Process A]

A compound [1] of the present invention can be prepared by reacting an amino compound of the formula [2]:

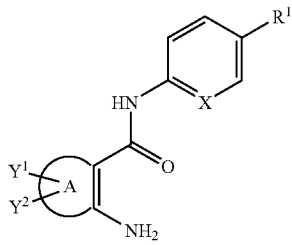

[2]

wherein the symbols are the same as defined above with a carboxylic acid compound of the formula [3]:

R²—OH [3]

wherein the symbols are the same as defined above, or a reactive derivative thereof at its carboxyl group.

[Process B]

A compound [1] of the present invention can also be prepared by reacting a compound [4]:

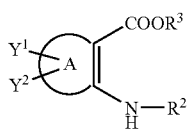

[4]

wherein R³ is a lower alkyl group and the other symbols are the same as defined above with a compound of the formula [5]:

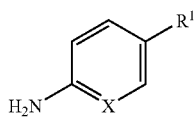

[5]

wherein the symbols are the same as defined above.

If necessary, a compound [1] prepared according to the Process [A] or [B] above can be adequately converted into another compound [1] through the mutual conversion by alkylation, reductive alkylation, amidation, sulfonyl-amidation, arylation, reduction, dealkylation, hydrolysis, quaternary amination, protection or deprotection of amino or carboxyl group, and the like.

[Manufacturing Process for Starting Materials: Preparation of Compound [2]]

The compound [2] can be prepared by reacting a compound of the formula [7]:

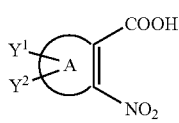

[7]

wherein the symbols are the same as defined above, or a reactive derivative thereof at its carboxyl group with a compound of the formula [5] to give a compound of the formula [6]:

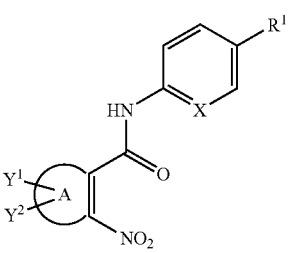

[6]

wherein the symbols are the same as defined above, and reducing the nitro group of compound [6].

The compound [2] can also be prepared by reacting a compound of the formula [10]:

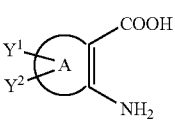

[10]

wherein the symbols are the same as defined above with a compound of the formula [11]:

L-COOZ [11]

wherein L is a leaving group and Z is a protecting group for carboxyl group to give a compound of the formula [9]:

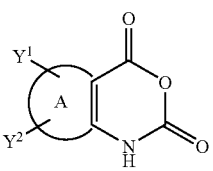

[9]

wherein the symbols are the same as defined above, subjecting the compound [9] to intramolecular cyclization to give a compound of the formula [8]:

[8]

wherein the symbols are the same as defined above, and reacting the compound [8] with a compound of the formula [5].

[Manufacturing Process for Starting Materials: Preparation of Compound [4]]

The compound [4] can be prepared by reacting a compound of the formula [12]:

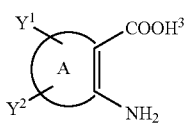

[12]

wherein the symbols are the same as defined above, with a compound [3] or a reactive derivative thereof at its carboxyl group.

The Processes [A] and [B] above can be carried out in the following manner.

[Process A]

The reaction where a compound [1] is prepared using compounds [2] and [3] can be carried out in a conventional manner for amidation. That is, the reaction can be carried out by reacting a compound [2] with a compound [3], a reactive derivative thereof at the carboxyl group, or a salt thereof in the presence or absence of a condensing agent, and if necessary, in the presence of an acid scavenger, in an appropriate solvent.

The condensing agent includes conventional agents such as N,N-dicyclohexylcarbodiimide (DCC), 1-ethyl-3-(3-dimethylaminopropyl)carbodiimide (EDC) or a hydrochloride thereof, carbonyldiimidazole (CDI), diphenylphosphorylazide (DPPA), diethyl cyanophosphonate (DEPC), and the like. Above all, DCC, EDC or a hydrochloride thereof is preferred.

Examples of the reactive derivative of compound [3] include those conventionally used in the condensation reaction, such as an acid halide, a mixed anhydride, a reactive ester, and the like. Examples of an activator that can be used for converting a compound [3] into the reactive derivative thereof include thionyl chloride, thionyl bromide, oxalyl chloride, N-hydroxylamines such as 1-hydroxysuccinimide, 1-hydroxybenzotriazole, and the like, and phenols such as p-nitrophenol, and the like. Above all, thionyl chloride, oxalyl chloride, 1-hydroxysuccinimide and 1-hydroxybenzotriazole are preferred. The acid chloride method is especially preferable.

Examples of the salt of a compound [3] or a reactive derivative of the compound [3] include a salt with an inorganic acid such as hydrochloric acid, hydrobromic acid, sulfuric acid, and the like.

An acid scavenger can also be used depending on the method to be employed, which includes inorganic or organic bases.

The present reaction may be facilitated when it is carried out in the presence of a base or by using such a base as a solvent.

Examples of inorganic bases include alkali metal carbonates (sodium carbonate, potassium carbonate, cesium carbonate, and the like), alkali earth metal carbonates (calcium carbonate, and the like), alkali metal hydrogen carbonates (sodium hydrogen carbonate, potassium hydrogen carbonate, and the like), alkali metal hydroxides (sodium hydroxide, potassium hydroxide, lithium hydroxide, and the like). Examples of organic bases include tri-lower alkylamines (triethylamine, tributylamine, diisopropyl-ethylamine, and the like), tertiary-amines (1,4-diazabicyclo[2.2.2]octane, 1,5-diazabicyclo[4.3.0]non-5-ene, 1,8-diazabicyclo[5.4.0]undec-7-ene, and the like), amines (N,N-dimethylaniline, N,N-diethylaniline, 4-dimethylaminopyridine, and the like), pyridine, lutidine, collidine, and the like. Above all, triethylamine, diisopropylethylamine, 4-dimethylaminopyridine, or pyridine is preferred for carrying out the reaction.

The present reaction can be carried out in the presence or absence of a solvent, preferably in the presence of a solvent.

Examples of the solvent include any inert solvent which does not disturb the reaction, such as halogenated hydrocarbons (chloroform, dichloromethane, dichloroethane, and the like), aromatic hydrocarbons (benzene, toluene, xylene, and the like), ethers (diethyl ether, diisopropyl ether, tetrahydrofuran, dioxane, 1,2-dimethoxyethane, and the like), esters (ethyl acetate, and the like), amides (N,N-dimethylformamide, N,N-dimethylacetamide, 1,3-dimethyl-2-imidazolidinone, and the like), nitrites (acetonitrile, and the like), dimethylsulfoxide, pyridine, lutidine, and the like, a mixed solvent comprising two or more of these solvents, if necessary, and also a mixture of any one(s) of these solvents and water. It is preferred to select any appropriate solvent depending on the method used. Above all, dichloromethane, chloroform, toluene, xylene, tetrahydrofuran, dioxane, N,N-dimethylformamide, N,N-dimethylacetamide, 1,3-dimethyl-2-imidazolidinone, pyridine, and the like are preferred, and dichloromethane, chloroform, N,N-dimethylformamide and pyridine are especially preferred. The present reaction can be carried out in a wide range of temperature from a temperature of under cooling to under heating. For example, the reaction can be preferably carried out at a temperature of −10° C. to the boiling point of the reaction mixture, especially from under ice-cooling to 60° C.

[Process B]

The step for preparing a compound [1] from compounds [4] and [5] can be carried out by heating the compounds [4] and [5] in the presence or absence of an appropriate solvent or by converting a compound [5] into the corresponding aluminium amide compound by the use of trimethyl alminium followed by reacting with a compound [4]. The method that uses an aluminium amide compound is preferred.

Examples of the solvent include any inert solvent which does not disturb the reaction, such as halogenated hydrocarbons (chloroform, dichloromethane, dichloroethane, and the like), aromatic hydrocarbons (benzene, toluene, xylene, and the like), ethers (diethyl ether, diisopropyl ether, tetrahydrofuran, dioxane, 1,2-dimethoxyethane, and the like), amides (N,N-dimethylformamide, N,N-dimethyl-acetamide, 1,3-dimethyl-2-imidazolidinone, and the like), hydrocarbons (hexane, and he like), dimethylsulfoxide, pyridine, lutidine, and the like, a mixed solvent comprising two or more of these solvents, if necessary. It is preferred to select any appropriate solvent depending on the method used. Above all, dichloromethane, chloroform, toluene, xylene, and hexane are preferred.

Examples of preferred reagents usable in a similar manner to trimethyl alminium include tri-lower alkyl alminium, sodium diethyldihydroaluminate, and the like.

The present reaction can be carried out in a wide range of temperature from a temperature of under cooling to under heating. For example, the reaction can be preferably carried out at a temperature of −10° C. to the boiling point of the reaction mixture, especially from under ice-cooling to 60° C.

Furthermore, after carrying out the Process [A] or [B], the objective compound [1] can also be obtained, if necessary, through a mutual conversion by conducting the following reaction(s), on condition that the resulting compounds of the formula [1] has one or more moieties available to further reaction(s), which moiety refers mainly to, for example, a protecting group for amine, alcoholic or phenolic OH, ester, carboxylic acid, nitro, halogen, and the like.

Among the mutual conversions, the reactions for alkylation, reductive alkylation, amidation, sulfonyl-amidation, arylation, reduction, dealkylation, hydrolysis, quaternary amination, protection and deprotection of amino or carboxyl group, which are conducted when needed, can be carried out as follows.

The alkylation can be carried out in a conventional manner, when needed. For example, this reaction can be carried out by reacting a compound [1] with an alkyl halide such as alkyl chloride, alkyl bromide, alkyl iodide, and the like in the presence or absence of a base in an appropriate solvent.

Examples of the bases usable include inorganic and organic bases. The inorganic bases include alkali metal carbonates (sodium carbonate, potassium carbonate, cesium carbonate, and the like), alkali metal hydrogen carbonates (sodium hydrogen carbonate, potassium hydrogen carbonate, and the like), alkali metal hydroxides (sodium hydroxide, potassium hydroxide, lithium hydroxide, and the like). Examples of organic bases include tri-lower alkylamines (triethylamine, tributylamine, diisopropylethylamine, and the like), tertiary-amines (1,4-diazabicyclo[2.2.2]octane, 1,5-diazabicyclo[4.3.0]non-5-ene, 1,8-diazabicyclo[5.4.0]-undec-7-ene, and the like), pyridine, lutidine, collidine, and the like Above all, alkali metal carbonates such as sodium carbonate, potassium carbonate and cesium carbonate, triethylamine, diisopropylethylamine, pyridine, and the like are preferred.

An alkali metal iodide such as lithium iodide, sodium iodide, potassium iodide, and the like can also be added, which may facilitate the reaction.

Any inert solvents which do not disturb the reaction can be used without limitation, and examples thereof include ethers (diethyl ether, diisopropyl ether, tetrahydrofuran, dioxane, 1,2-dimethoxyethane, and the like), amides (N,N-dimethylformamide, N,N-dimethylacetamide, 1,3-dimethyl-2-imidazolidinone, and the like), nitrites (acetonitrile, and the like), alcohols (methanol, ethanol, propanol, and the like), dimethylsulfoxide, pyridine, lutidine, and the like, and a mixed solvent comprising two or more of these solvents, if necessary. It is preferred to select any appropriate solvent depending on the method used. Above all, tetrahydrofuran, N,N-dimethylformamide, N,N-dimethylacetamide, 1,3-dimethyl-2-imidazolidinone, acetonitrile, ethanol, dimethylsulfoxide, and the like, are preferred and N,N-dimethylformamide, acetonitrile, ethanol, and a mixed solvent thereof are more preferred.

The present reaction can be carried out in a wide range of temperature from a temperature of under cooling to under heating, preferably at −10° C. to the boiling point of the reaction mixture.

The reductive alkylation can be carried out in a conventional manner, when needed. For example, this reaction can be carried out by reacting a compound [1] with a corresponding carbonyl compound in the presence of an appropriate metal hydride reducing agent, or under the condition for catalytic reduction in the presence of an appropriate metal catalyst, in an appropriate solvent.

In the reaction, any conventional metal hydride reducing agents can be used without limitation; however, reducing agents which do not affect the amide bonds and the like, such as sodium borohydride, sodium triacetoxy borohydride, sodium cyano borohydride, and the like are preferred.

Besides, organic acids such as acetic acid, and the like or mineral acids such as hydrochloric acid, and the like can also be added to the present reaction, which may facilitate the reaction.

Furthermore, when the compound [1] used is an amine in the form of a salt with a mineral acid such as hydrochloric acid, and the like, an appropriate neutralizing agent such as an organic base (e.g., triethylamine) or an alkali metal acetate (e.g., sodium acetate) may be added to the reaction, which may facilitate the reaction.

Any inert solvents which do not disturb the reaction can be used without limitation, and examples thereof include halogenated hydrocarbons (chloroform, dichloromethane, dichloroethane, and the like), ethers (diethyl ether, diisopropyl ether, tetrahydrofuran, dioxane, 1,2-dimethoxyethane, and the like), amides (N,N-dimethylformamide, N,N-dimethylacetamide, 1,3-dimethyl-2-imidazolidinone, and the like), nitrites (acetonitrile, and the like), aromatic hydrocarbons (benzene, toluene, xylene, and the like), alcohols (methanol, ethanol, propanol, and the like), water, and a mixed solvent comprising two or more of these solvents, if necessary. It is preferred to select any appropriate solvent depending on the method used. Above all, dichloromethane, dichloroethane, tetrahydrofuran, 1,2-dimethoxyethane, methanol, ethanol, propanol, and the like are preferred, and dichloromethane, dichloroethane and tetrahydrofuran are especially preferred.

The reaction can be carried out in a wide range of temperature from a temperature of under cooling to under heating. For example, the reaction can be preferably carried out at a temperature of −10° C. to the boiling point of the reaction mixture, especially from under ice-cooling to the boiling point of the mixture.

The present reaction can similarly be carried out according to the catalytic hydrogenation in the presence of a metal catalyst. Examples of the metal catalyst include palladium-carbon, platinum-carbon, platinum oxide, Raney Nickel, and the like.

Besides, organic acids such as acetic acid, and the like or mineral acids such as hydrochloric acid, and the like can also be added to the present reaction, which may facilitate the reaction.

Furthermore, when the compound [1] used is an amine in the form of a salt with a mineral acid such as hydrochloric acid, and the like, an appropriate neutralizing agent such as an organic base (e.g., triethylamine) or an alkali metal acetate (e.g., sodium acetate) may be added to the reaction, which may facilitate the reaction.

Any inert solvents which do not disturb the reaction can be used without limitation, and examples thereof include ethers (diethyl ether, diisopropyl ether, tetrahydrofuran, dioxane, 1,2-dimethoxyethane, and the like), amides (N,N-dimethylformamide, N,N-dimethylacetamide, 1,3-dimethyl-2-imidazolidinone, and the like), aromatic hydrocarbons (benzene, toluene, xylene, and the like), alcohols (methanol, ethanol, propanol, and the like), water, and a mixed solvent comprising two or more of these solvents, if necessary. It is preferred to select any appropriate solvent depending on the method used. Above all, tetrahydrofuran, N,N-dimethylformamide, methanol, ethanol, and the like are preferred, and tetrahydrofuran, methanol, ethanol, and the like are especially preferred.

The reaction can be carried out in a wide range of temperature from a temperature of under cooling to under heating. For example, the reaction can be preferably carried out at a temperature of −10° C. to the boiling point of the reaction mixture, especially from under ice-cooling to room temperature.

The amidation can be carried out in a conventional manner, for example, in a manner similar to the above-mentioned reaction between a compound [2] and a compound [3], when needed.

The sulfonylamidation can be carried out in a conventional manner, when needed. For example, this reaction can be carried out by reacting a compound [1] with an optionally substituted alkylsulfonic acid halide in the presence or absence of a base in an appropriate solvent. For the reaction, similar acid scavenger, solvent and reaction temperature to those used in the amidation reaction between a compound [2] and a compound [3] above can be employed.

The arylation can be carried out in a conventional manner, when needed. For example, the reaction can be carried out by reacting a compound [1] with a halogenated aryl compound in the presence or absence of an appropriate base in an appropriate solvent.

Examples of the bases usable include inorganic and organic bases. The inorganic bases include alkali metal carbonates (sodium carbonate, potassium carbonate, cesium carbonate, and the like), alkali metal hydrogen carbonates (sodium hydrogen carbonate, potassium hydrogen carbonate, and the like), and the like. Examples of organic bases include tri-lower alkylamines (triethylamine, tributylamine, diisopropylethylamine, and the like), tert-amines (1,4-diazabicyclo[2.2.2]octane, 1,5-diazabicyclo[4.3.0]-non-5-ene, 1,8-diazabicyclo[5.4.0]undec-7-ene, and the like), amines (N,N-dimethylaniline, N,N-diethylaniline, 4-dimethylaminopyridine, and the like), pyridine, lutidine, collidine, and the like. Above all, triethylamine, diisopropylethylamine, potassium carbonate, and the like are preferred.

The present reaction can be carried out in the presence or absence of a solvent, preferably in the presence of a solvent.

Any inert solvents which do not disturb the reaction can be used without limitation, and examples thereof include aromatic hydrocarbons (benzene, toluene, xylene, and the like), ethers (diethyl ether, diisopropyl ether, tetrahydrofuran, dioxane, 1,2-dimethoxyethane, and the like), amides (N,N-dimethylformamide, N,N-dimethylacetamide, 1,3-dimethyl-2-imidazolidinone, and the like), nitriles (acetonitrile, and the like), alcohols (methanol, ethanol, propanol, butanol, and the like), dimethylsulfoxide, pyridine, lutidine, and the like, and a mixed solvent comprising two or more of these solvents, if necessary. Above all, xylene, tetrahydrofuran, N,N-dimethylformamide, N,N-dimethylacetamide, 1,3-dimethyl-2-imidazolidinone, ethanol, butanol, and the like are preferred and tetrahydrofuran, N,N-dimethylacetamide and butanol are more preferred.

The reaction can be carried out in a wide range of temperature from a temperature of under cooling to under heating. For example, the reaction can be preferably carried out at a temperature of −10° C. to the boiling point of the reaction mixture, especially from room temperature to the boiling point of the reaction mixture. It can also be carried out according to the palladium coupling reaction.

The reduction can be carried out in a conventional manner, when needed. For example, the reaction can be carried out by reacting a compound [1] with an appropriate reducing agent, or with hydrogen in the presence of a metal catalyst in an appropriate solvent.

In the reaction, any conventional reducing agents can be used without limitation; however, metal hydride reducing agents such as lithium aluminium hydride, lithium borohydride, sodium borohydride, and the like, metals such as zinc, iron, stannum, and the like, and metal salts such as tin chloride, and the like are preferred, and metals such as stannum, and the like and metal salts such as tin chloride, and the like are more preferred. In the catalytic hydrogenation, any conventional metal catalysts can be used without limitation; however, palladium-carbon, Raney Nickel, Raney Cobalt, platinum oxide, and the like are preferred and metals such as Raney Nickel, and the like are more preferred. Furthermore, depending on the method used, the reaction can sometimes be facilitated when it is carried out under an acidic condition in the co-existence of a mineral acid such as hydrochloric acid, and the like In the reaction where a metal hydride reducing agent is used, any inert solvents which do not disturb the reaction can be used without limitation, and examples thereof include ethers (diethyl ether, diisopropyl ether, tetrahydrofuran, dioxane, 1,2-dimethoxyethane, and the like), amides (N,N-dimethylformamide, N,N-dimethylacetamide, 1,3-dimethyl-2-imidazolidinone, and the like), aromatic hydrocarbons (benzene, toluene, xylene, and the like), alcohols (methanol, ethanol, propanol, and the like), water, and the like, and a mixed solvent comprising two or more of these solvents, if necessary. It is preferred to select any appropriate solvent depending on the method used.

In the reaction where a metal such as zinc, iron, stannum, and the like, or a metal salt such as tin chloride, and the like is used, any inert solvents which do not disturb the reaction can be used without limitation, and examples thereof include water, alcohols (methanol, ethanol, propanol, and the like), esters (ethyl acetate, and the like), ethers (diethyl ether, diisopropyl ether, tetrahydrofuran, 1,2-dimethoxyethane, and the like), amides (N,N-dimethylformamide, N,N-dimethylacetamide, 1,3-dimethyl-2-imidazolidinone, and the like), nitrites (acetonitrile, and the like), aromatic hydrocarbons (benzene, toluene, xylene, and the like), and a mixed solvent comprising two or more of these solvents, if necessary. It is preferred to select any appropriate solvent depending on the method used. Above all, ethyl acetate, water, or a mixed solvent comprising water and an alcohol, an ether, an amide, a nitrile and the like is preferred.

In the reaction where hydrogenation is carried out in is the presence of a metal catalyst, any inert solvents which do not disturb the reaction can be used without limitation, and examples thereof include alcohols, ethers, aliphatic hydrocarbons, aromatic hydrocarbons, amides, esters (ethyl acetate, and the like), organic acids (formic acid, acetic acid, propionic acid, trifluoroacetic acid, and the like), and a mixed solvent comprising two or more of these solvents, if necessary. It is preferred to select any appropriate solvent depending on the method used.

The present reaction can be carried out in a wide range of temperature from a temperature of under cooling to under heating. For example, the reaction can be preferably carried out at a temperature of −10° C. to the boiling point of the reaction mixture.

The hydrogen pressure used in the catalytic hydrogenation reaction is generally about 1-100 atm.

The reaction time for the present reaction varies depending on the kind of the reducing agent or the activity of the catalyst used; however, it is generally between about 10 minutes and 24 hours.

The dealkylation can be carried out in a conventional manner, when needed. For example, this reaction can be carried out by reacting a compound [1] with an appropriate dealkylating agent in an appropriate solvent or without solvent.

Any conventional alkylating agents can be used without limitation, and preferred examples thereof include boron tribromide, boron trichloride, iodotrimethylsilane, aluminium (III) chloride, pyridinium chloride, and the like, and boron tribromide, iodotrimethylsilane, and the like are preferred.

Any inert solvents which do not disturb the reaction can be used without limitation, and examples thereof include halogenated hydrocarbons (chloroform, dichloromethane, dichloroethane, and the like), amides (N,N-dimethylformamide, N,N-dimethylacetamide, 1,3-dimethyl-2-imidazolidinone, and the like), nitrites (acetonitrile, and the like), and a mixed solvent comprising two or more of these solvents, if necessary. It is preferred to select any appropriate solvent depending on the method used.

The reaction can be carried out in a wide range of temperature from a temperature of under cooling to under heating, preferably from −78° C. to the boiling point of the reaction mixture.

The hydrolysis can be carried out in a conventional manner, when needed.

The quaternary amination can be carried out in a conventional manner, when needed. This reaction can be conducted in a similar manner to the above-mentioned alkylation.

The protection of an amino or a carboxy group, or deprotection of the protected group can be carried out, when needed, according to any of known methods.

[Manufacturing Process for Starting Materials: Preparation of compound [2]]

The step for preparing the compound [6] by reacting the compound [7] or a reactive derivative thereof at its carboxyl group with the compound [5] can be carried out in a similar manner to the step where the compounds [2] and [3] are reacted.

The next step for reducing the nitro group to give the compound [2] can be carried out in a similar manner to the above-mentioned reduction.

The step for preparing the compound [9] by reacting the compound [10] with the compound [11] can be carried out in a similar manner to the step where the compounds [2] and [3] are reacted.

The step for intramolecular cyclization of the compound [9] to give the compound [8] can be carried out in an appropriate solvent in the presence or absence of a condensing agent, after converting the compound [9] into reactive derivative by using an activator, if necessary, and in the presence or absence of an acid scavenge.

The condensing agent includes conventional agents such as N,N-dicyclohexylcarbodiimide (DCC), 1-ethyl-3-(3-dimethylaminopropyl)carbodiimide (EDC) or a hydrochloride thereof, carbonyldiimidazole (CDI), diphenylphosphorylazide (DPPA), diethyl cyanophosphonate (DEPC), and the like. Above all, DCC, EDC or a hydrochloride thereof is preferred.

Examples of the reactive derivative of compound [9] include those conventionally used in the condensation reaction, such as an acid halide, a mixed anhydride, a reactive ester, and the like. Examples of an activator that can be used for converting the compound [9] into the reactive derivative thereof include thionyl chloride, oxalyl chloride, and the like. Above all, acid chloride method can be used conveniently.

An acid scavenger can also be used depending on the method to be employed, which includes inorganic or organic bases.

The present reaction may be facilitated when it is carried out in the presence of a base or by using such a base as a solvent.

Examples of inorganic bases include alkali metal carbonates (sodium carbonate, potassium carbonate, cesium carbonate, and the like), alkali earth metal carbonates (calcium carbonate, and the like), alkali metal hydrogen carbonates (sodium hydrogen carbonate, potassium hydrogen carbonate, and the like), alkali metal hydroxides (sodium hydroxide, potassium hydroxide, lithium hydroxide, and the like). Examples of organic bases include tri-lower alkylamines (triethylamine, tributylamine, diisopropyl-ethylamine, and the like), tertiary-amines (1,4-diazabicyclo[2.2.2]octane, 1,5-diazabicyclo[4.3.0]non-5-ene, 1,8-diazabicyclo[5.4.0]undec-7-ene, and the like), amines (N,N-dimethylaniline, N,N-diethylaniline, 4-dimethylaminopyridine, and the like), pyridine, lutidine, collidine, and the like. Above all, triethylamine, diisopropylethylamine, 4-dimethylaminopyridine, or pyridine is preferred for carrying out the reaction.

The present reaction can be carried out in the presence or absence of a solvent, preferably in the presence of a solvent.

Examples of the solvent include any inert solvent which does not disturb the reaction, such as halogenated hydrocarbons (chloroform, dichloromethane, dichloroethane, and the like), aromatic hydrocarbons (benzene, toluene, xylene, and the like), ethers (diethyl ether, diisopropyl ether, tetrahydrofuran, dioxane, 1,2-dimethoxyethane, and the like), esters (ethyl acetate, and the like), amides (N,N-dimethylformamide, N,N-dimethylacetamide, 1,3-dimethyl-2-imidazolidinone, and the like), nitriles (acetonitrile, and the like), dimethylsulfoxide, pyridine, lutidine, and the like, a mixed solvent comprising two or more of these solvents, if necessary, and also a mixture of any one(s) of these solvents and water. It is preferred to select any appropriate solvent depending on the method used. Above all, dichloromethane, chloroform, toluene, xylene, tetrahydrofuran, dioxane, N,N-dimethylformamide, N,N-dimethylacetamide, 1,3-dimethyl-2-imidazolidinone, pyridine, and the like are preferred, and dichloromethane, chloroform, N,N-dimethylformamide and pyridine are especially preferred. The present reaction can be carried out in a wide range of temperature from a temperature of under cooling to under heating. For example, the reaction can be preferably carried out at a temperature of −10° C. to the boiling point of the reaction mixture, especially from under ice-cooling to 60° C.

The step for preparing the compound [2] by reacting a compound [8] with a compound [5] can be carried out in a similar manner to the step where the compounds [4] and [5] are reacted.

[Manufacturing Process for Starting Materials: Preparation of compound [4]]

The step for preparing the compound [4] by reacting the compound [12] with the compound [3] or a reactive derivative thereof at its carboxyl group can be carried out in a similar manner to the step where the compounds [2] and [3] are reacted.

The compounds of the present invention thus produced can be isolated and purified by a procedure well known in the field of organic chemistry such as recrystallization, column chromatography, and the like.

The present compound [1] or a pharmaceutically acceptable salt thereof has an excellent inhibitory effect on FXa, and hence is useful in the prevention and treatment of various disorders caused by thrombi and emboli in a mammal (e.g., human, monkey, rabbit, dog, cat, pig, horse, bull, mouse, rat, guinea pig, and the like), which disorders include, for example, stable angina pectoris, unstable angina pectoris, cerebral thrombosis, cerebral infarction, cerebral embolism, transient ischemic attack (TIA), ischemic cerebrovascular disease such as cerebrovascular spasm after subarachnoid hemorrhage, ischemic heart disease caused by coronary artery thrombogenesis, congestive chronic heart failure, myocardial infarction, acute myocardial infarction, pulmonary infarction, pulmonary embolism, pulmonary vascular disorders, economy-class syndrome, kidney disease (diabetic renal disease, chronic glomerulonephritis, IgA nephropathy, and the like), thrombogenesis with atherosclerosis, peripheral arterial occlusion, peripheral venous occlusion, Buerger's disease, deep vein thrombosis, disseminated intravascular coagulation (DIC), thrombogenesis after implantation of a synthetic vascular prosthesis or replacement of artificial heart valve or joint, intermittent claudication, thrombogenesis and reocclusion after blood circulation reconstruction such as percutaneous transluminal coronary angioplasty (PTCA) or percutaneous transluminal coronary artery recanalization (PTCR), systemic inflammatory response syndrome (SIRS), multiple organ failure (MODS), thrombogenesis in extracorporeal circulation, blood coagulation in case of blood drawing, diabetic circulatory disturbance, graft rejection, organ protection and improvement of function in case of transplantation, and the like The present compound is characterized in that it shows excellent inhibitory effect on FXa, decreased toxicity, and causes few side effects (bleeding, and the like) that are seen in the existing anticoagulants.

When a FXa inhibitor has a small distribution volume (internal medicine/blood concentration), it would be substantially free of side effects such as phospholipidosis, hepatotoxicity, and the like Accordingly, FXa inhibitors, especially those having the distribution volume of 0.1-3.0 L/kg and the FXa inhibitory effect with the $IC_{50}$ value of 100 nM or below are substantially free of side effects such as phospholipidosis, hepatotoxicity, and the like, and useful as a medicament for treating thrombosis.

The present compound [1] or a pharmaceutically acceptable salt thereof can be formulated into a pharmaceutical composition comprising a therapeutically effective amount of the compound [1] and a pharmaceutically acceptable carrier therefor. The pharmaceutically acceptable carriers include diluents, binders (e.g., syrup, gum arabic, gelatine, sorbit, tragacanth, polyvinylpyrrolidone), excipients (e.g., lactose, sucrose, corn starch, potassium phosphate, sorbit, glycine), lubricants (e.g., magnesium stearate, talc, polyethylene glycol, silica), disintegrants (e.g., potato starch) and wetting agents (e.g., sodium lauryl sulfate), and the like The compound [1] of the present invention or a pharmaceutically acceptable salt thereof can be administered orally or parenterally, and be used as an appropriate pharmaceutical preparation. Examples of an appropriate preparation for oral administration include solid preparations (tablets, granules, capsules, powders, and the like), solutions, suspensions and emulsions. Examples of an appropriate preparation for parenteral administration include suppository, injections or preparation for continuous infusion prepared using distilled water for injection, physiological saline or aqueous glucose solution, and the like, or inhalant.

The dose of the compound [1] or a pharmaceutically acceptable salt thereof of the present invention may vary depending on the administration routes, and the age, weight and condition of the patient, or the kind or severity of the disease, it is usually in the range of about 0.1 to 50 mg/kg/day, preferably about 0.1 to 30 mg/kg/day.

EXAMPLES

The present invention will be illustrated in detail by Examples and Reference Examples, but should not be construed to be limited thereto.

Example 1

N-(5-Chloropyridin-2-yl)-5-methoxy-2-({[trans-4-(3-oxomorpholin-4-yl)cyclohexyl]carbonyl}amino)benzamide

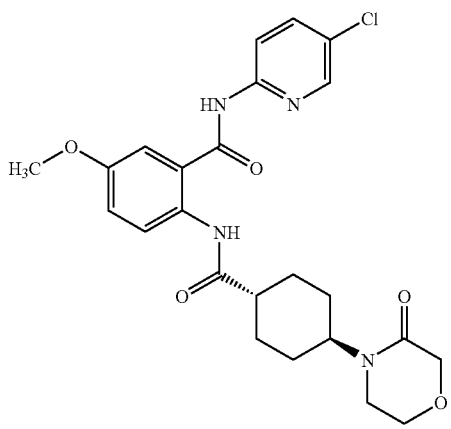

Trans-4-(3-oxomorpholin-4-yl)cyclohexanecarboxylic acid (120 mg) obtained in Reference Example 4 is dissolved in chloroform (3 ml), and thereto are added 1M thionyl chloride solution in chloroform (540 μl) and N,N-dimethylformamide (one drop), and the mixture is stirred at room temperature for 7 hours. To the resulting reaction solution are added 2-amino-N-(5-chloropyridin-2-yl)-5-methoxybenzamide (111 mg) and pyridine (1 ml), and the mixture is stirred at room temperature overnight. To the mixture is poured saturated aqueous sodium hydrogen carbonate solution, and the mixture is extracted with chloroform. The organic layer is concentrated under reduced pressure, and the resulting residue is purified by NH-silica gel column chromatography (eluent: n-hexane/ethyl acetate=1/1, then ethyl acetate) to give the title compound (158 mg). APCI-MS M/Z: 487/489[M+H]$^+$

Example 2 t-Butyl 4-{[(5-chloropyridin-2-yl)amino]-carbonyl}-3-({[trans-4-(3-oxomorpholin-4-yl)cyclohexyl]-carbonyl}amino)benzoate

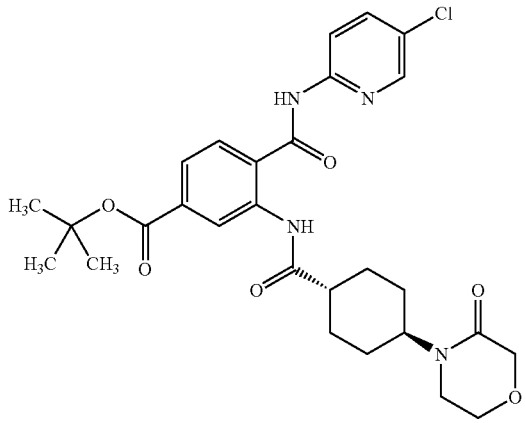

(1) 4-(t-Butoxycarbonyl)-2-nitrobenzoic acid (1.0 g) is dissolved in tetrahydrofuran (50 ml), and thereto is added 28% sodium methoxide in methanol (0.72 g). After pouring toluene, the mixture is concentrated under reduced pressure. The resulting residue is suspended in chloroform (50 ml), and thereto are added oxalyl chloride (489 μl) and N,N-dimethylformamide (2 drops) followed by stirring at room temperature for 3 hours. The reaction solution is concentrated under reduced pressure, and chloroform (20 ml) is poured to the residue to give a suspension. 5-Chloro-2-aminopyridine (480 mg) and pyridine (453 μl) are dissolved in chloroform (30 ml), and the solution is ice-cooled. To the solution is added dropwise the suspension prepared above. The reaction solution is stirred at room temperature for 8 hours and concentrated under reduced pressure. The residue is diluted with ethyl acetate, washed successively with 10% aqueous potassium hydrogen sulfate solution, saturated aqueous sodium hydrogen carbonate solution and saturated brine, dried over magnesium sulfate, and evaporated to remove the solvent under reduced pressure. The resulting residue is purified by silica gel column chromatography (eluent: n-hexane/ethyl acetate=4/1) to give t-butyl 4-{[(5-chloropyridin-2-yl)amino]carbonyl}-3-nitrobenzoate (803 mg). APCI-MS M/Z: 378[M+H]$^+$ (2) t-Butyl 4-{[(5-chloropyridin-2-yl)amino]-carbonyl}-3-nitrobenzoate (3.2 g) obtained in Example 2(1) is dissolved in tetrahydrofuran (50 ml) and thereto is added Raney nickel, and the mixture is stirred at room temperature under hydrogen pressure (3 atm.) overnight. The insoluble materials are removed by filtration on Celite and the filtrate is concentrated under reduced pressure. The residue is purified by silica gel column chromatography (eluent: chloroform/ethyl acetate=20/1) to give t-butyl 3-amino-4-{[(5-chloropyridin-2-yl)amino]carbonyl}benzoate (2.3 g). APCI-MS M/Z: 348[M+H]$^+$ (3) t-Butyl 3-amino-4-{[(5-chloropyridin-2-yl)-amino]carbonyl}benzoate (278 mg) obtained in Example 2(2) is treated in a similar manner to Example 1 to give the title compound (190 mg).

APCI-MS M/Z: 557/559[M+H]$^+$

Example 3

4-{[(5-Chloropyridin-2-yl)amino]carbonyl}-3-({[trans-4-(3-oxomorpholin-4-yl)cyclohexyl]carbonyl}amino)-benzoic acid

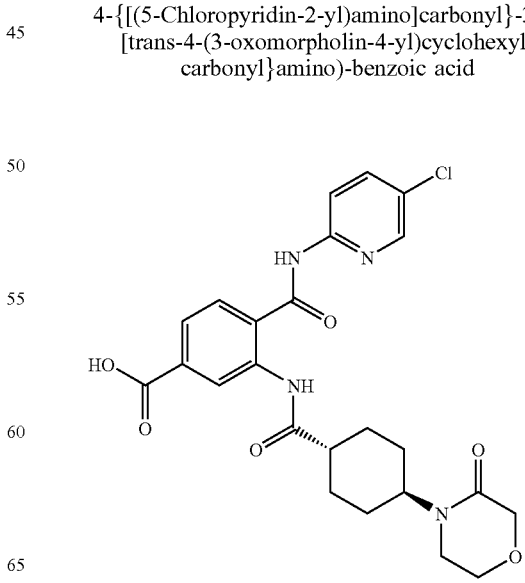

t-Butyl 4-{[(5-chloropyridin-2-yl)amino]carbonyl}-3-({[trans-4-(3-oxomorpholin-4-yl)cyclohexyl]carbonyl}amino)-benzoate (293 mg) obtained in Example 2 is dissolved in chloroform (10 ml), and thereto is added 4N hydrogen chloride-dioxane solution (10 ml) followed by stirring at room temperature for 3 days. To the reaction solution is poured diisopropyl ether, and the solid precipitates are collected by filtration to give the title compound (280 mg). ESI-MS M/Z: 499/501[M−H]⁻

Example 4
N¹-(5-Chloropyridin-2-yl)-N⁴,N⁴-dimethyl-2-({[trans-4-(3-oxomorpholin-4-yl)cyclohexyl]carbonyl}amino)-terephthalamide

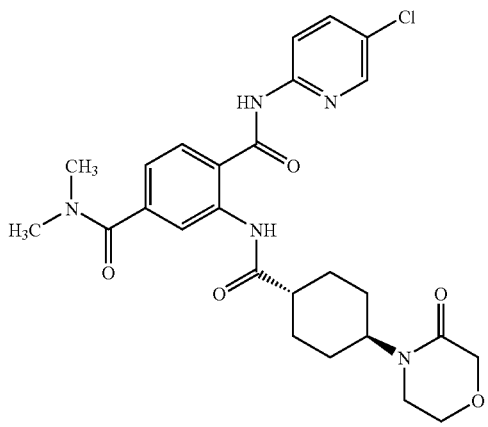

4-{[(5-Chloropyridin-2-yl)amino]carbonyl}-3-({[trans-4-(3-oxomorpholin-4-yl)cyclohexyl]carbonyl}amino)benzoic acid (50 mg) obtained in Example 3 is dissolved in pyridine (1 ml), and thereto are added dimethylamine hydrochloride (20 mg), 1-hydroxybenzotriazole (27 mg) and 1-ethyl-3-(3-dimethylaminopropyl)carbodiimide hydrochloride (40 mg), followed by stirring at room temperature for 20 hours. To the reaction solution is poured saturated aqueous sodium hydrogen carbonate solution, and the mixture is extracted with chloroform. The organic layer is concentrated under reduced pressure, and the resulting residue is purified by NH-silica gel column chromatography (eluent: n-hexane/ethyl acetate=1/1, then ethyl acetate) to give the title compound (28 mg). APCI-MS M/Z: 528/530[M+H]⁺

Example 5
N-(5-Chloropyridin-2-yl)-2-({[trans-4-(3-oxomorpholin-4-yl)cyclohexyl]carbonyl}amino)-4-(trifluoromethyl)benzamide

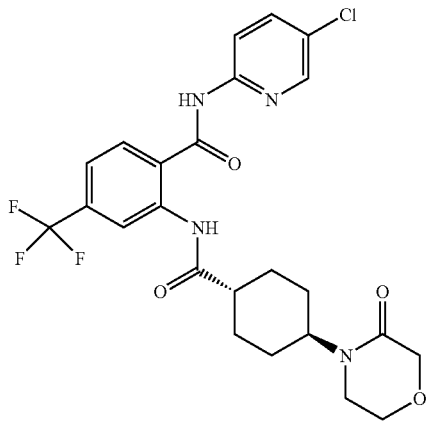

(1) 2-Nitro-4-(trifluoromethyl)benzoic acid (3.0 g) is suspended in chloroform (25 ml), and thereto are added oxalyl chloride (1.67 ml) and N,N-dimethylformamide (2 drops) followed by stirring at room temperature for 3 hours. The reaction solution is concentrated under reduced pressure, and to the residue is poured chloroform (20 ml) to obtain a suspension. Chloroform (30 ml) is added to 5-chloro-2-aminopyridine (1.56 g) and pyridine (1.55 ml), and the solution is ice-cooled. To the solution is added dropwise the suspension prepared above. The reaction solution is stirred at room temperature for 8 hours and concentrated under reduced pressure. The residue is diluted with ethyl acetate, washed successively with 10% aqueous potassium hydrogen sulfate solution, saturated aqueous sodium hydrogen carbonate solution and saturated brine, dried over magnesium sulfate, and evaporated to remove the solvent under reduced pressure. The resulting residue is suspended into n-hexane, filtered and dried to give N-(5-chloropyridin-2-yl)-2-nitro-4-(trifluoromethyl)-benzamide (4.73 g). APCI-MS M/Z: 346/348[M+H]⁺

(2) N-(5-Chloropyridin-2-yl)-2-nitro-4-(trifluoro-methyl)benzamide (4.73 g) obtained in Example 5(1) is treated in a similar manner to Example 2(2) to give 2-amino-N-(5-chloropyridin-2-yl)-4-(trifluoromethyl)benzamide (1.55 g). APCI-MS M/Z: 316/318[M+H]⁺

(3) 2-Amino-N-(5-chloropyridin-2-yl)-4-(trifluoro-methyl)benzamide (126 mg) obtained in Example 5(2) is treated in a similar manner to Example 1 to give the title compound (183 mg). APCI-MS M/Z: 525/527[M+H]⁺

Example 6

N-(5-Chloropyridin-2-yl)-2-({[trans-4-(2-oxopyrrolidin-1-yl)cyclohexyl]carbonyl}amino)-4-(trifluoromethyl)benzamide

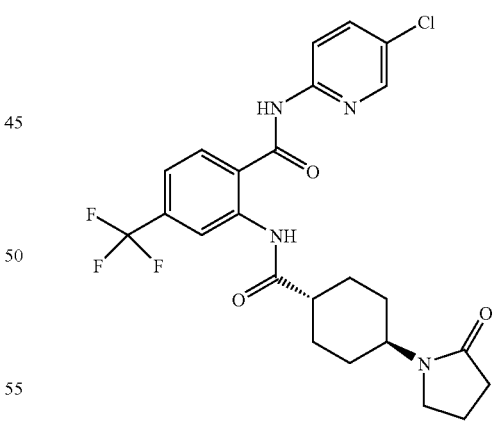

2-Amino-N-(5-chloropyridin-2-yl)-4-(trifluoromethyl)-benzamide (72 mg) obtained in Example 5(2) and trans-4-(2-oxopyrrolidin-1-yl)cyclohexanecarboxylic acid (63 mg) obtained in Reference Example 2 are treated in a similar manner to Example 1 to give the title compound (95 mg). APCI-MS M/Z: 509/511[M+H]⁺

Example 7

N-(5-Chloropyridin-2-yl)-4,5-dimethoxy-2-({[trans-4-(3-oxomorpholin-4-yl)cyclohexyl]carbonyl}-amino)benzamide

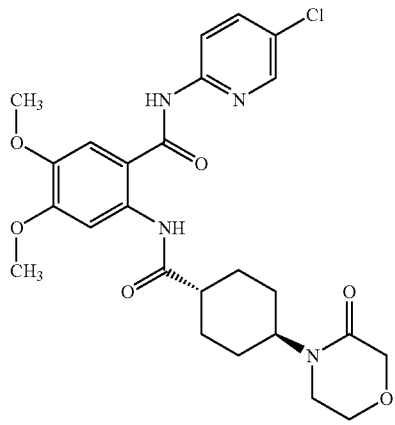

(1) N-(5-Chloropyridin-2-yl)-4,5-dimethoxy-2-nitro-benzamide (2.73 g) is treated in a similar manner to Example 2(2) to obtain 2-amino-N-(5-chloropyridin-2-yl)-4,5-dimethoxybenzamide (2.53 g). APCI-MS M/Z: 308/310[M+H]$^+$ (2) 2-Amino-N-(5-chloropyridin-2-yl)-4,5-dimethoxy-benzamide (123 mg) obtained in Example 7(2) is treated in a similar manner to Example 1 to give the title compound (163 mg). APCI-MS M/Z: 517/519[M+H]$^+$

Examples 8-33

The corresponding amino compounds and carboxylic acids are treated in a similar manner to Example 1 to give the following compounds.

| Ex. No. | Structure | Physicochemical Properties |
| --- | --- | --- |
| 8 | 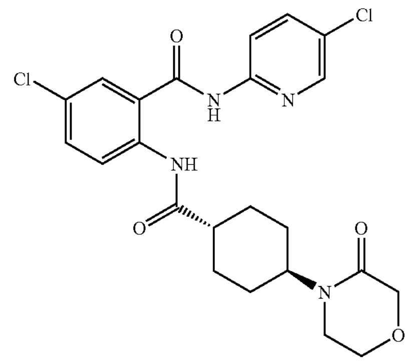 | APCI-MS M/Z: 491/493 [M + H]$^+$ |
| 9 | 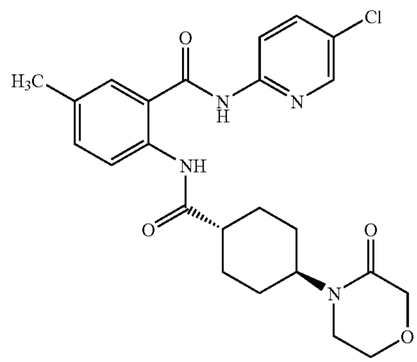 | APCI-MS M/Z: 471/473 [M + H]$^+$ |

-continued

| Ex. No. | Structure | Physicochemical Properties |
| --- | --- | --- |
| 10 | 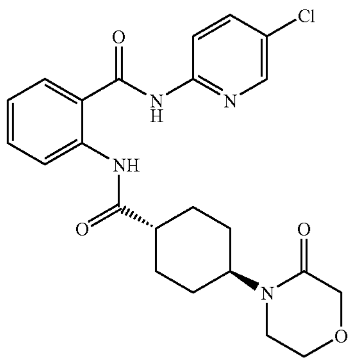 | APCI-MS M/Z: 457/459 [M + H]+ |
| 11 | 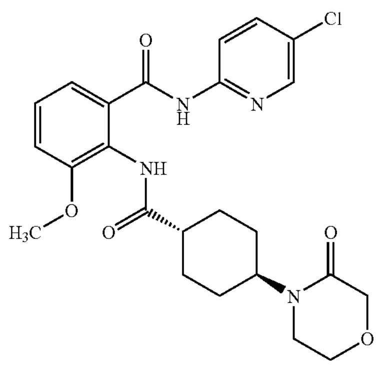 | APCI-MS M/Z: 487/489 [M + H]+ |
| 12 | 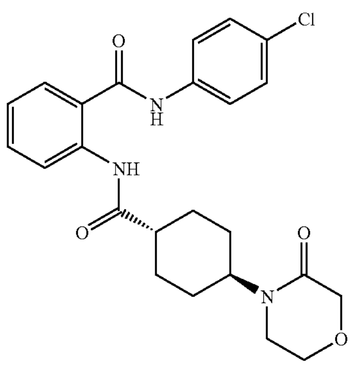 | APCI-MS M/Z: 456/458 [M + H]+ |
| 13 | 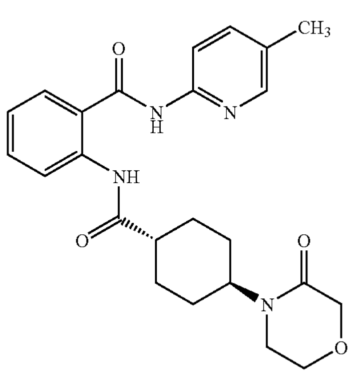 | APCI-MS M/Z: 437 [M + H]+ |

-continued

| Ex. No. | Structure | Physicochemical Properties |
|---|---|---|
| 14 | 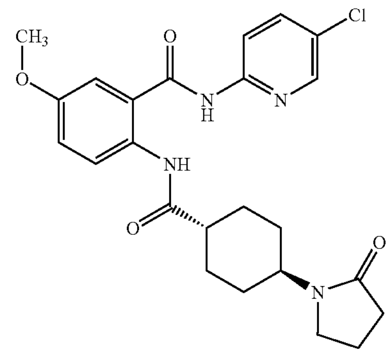 | APCI-MS M/Z: 471/473 $[M + H]^+$ |
| 15 | 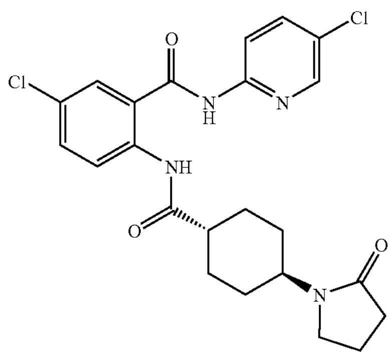 | APCI-MS M/Z: 475/477 $[M + H]^+$ |
| 16 | 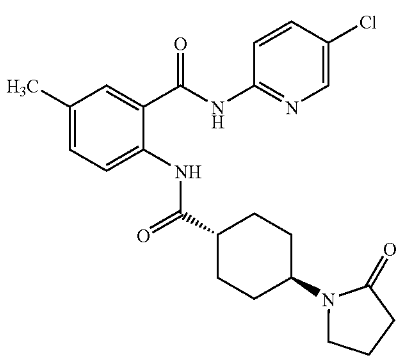 | APCI-MS M/Z: 455/457 $[M + H]^+$ |
| 17 | 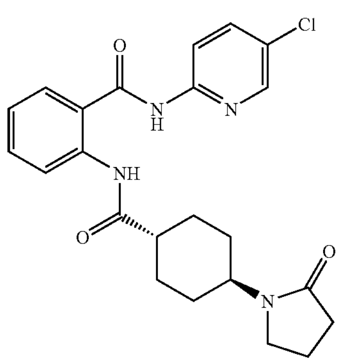 | APCI-MS M/Z: 441/443 $[M + H]^+$ |

-continued

| Ex. No. | Structure | Physicochemical Properties |
|---|---|---|
| 18 | 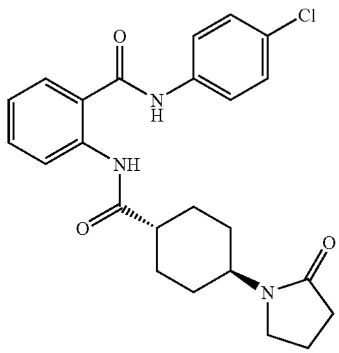 | APCI-MS M/Z: 440/442 [M + H]+ |
| 19 | 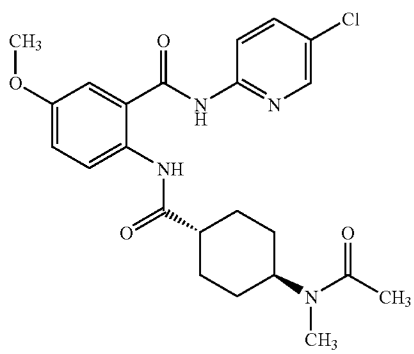 | APCI-MS M/Z: 459/461 [M + H]+ |
| 20 | 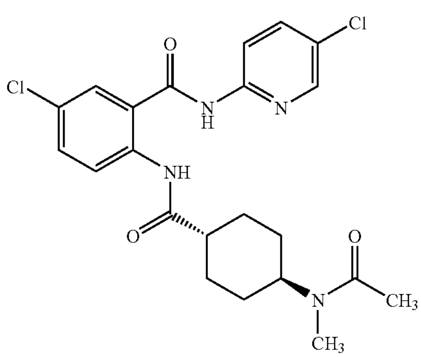 | APCI-MS M/Z: 463/465 [M + H]+ |
| 21 | 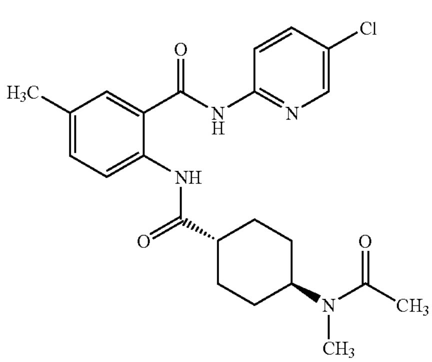 | APCI-MS M/Z: 443/445 [M + H]+ |

-continued

| Ex. No. | Structure | Physicochemical Properties |
|---|---|---|
| 22 | 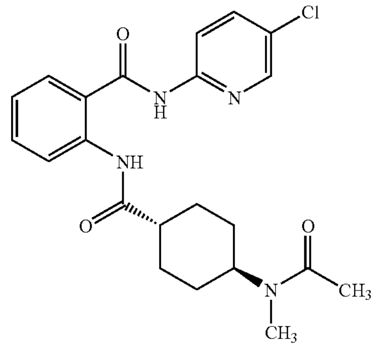 | APCI-MS M/Z: 429/431 [M + H]+ |
| 23 | 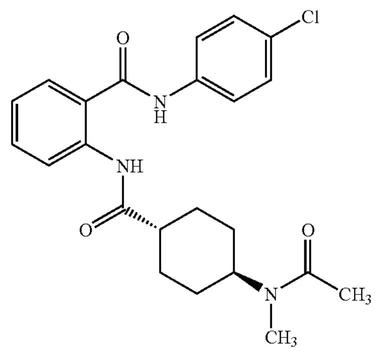 | APCI-MS M/Z: 428/430 [M + H]+ |
| 24 | 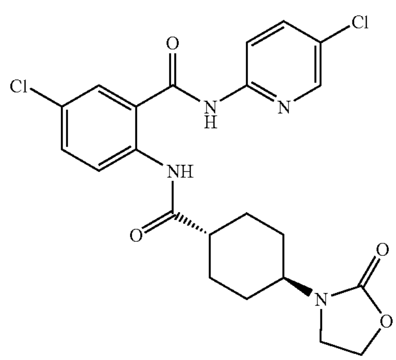 | APCI-MS M/Z: 477/479 [M + H]+ |
| 25 | 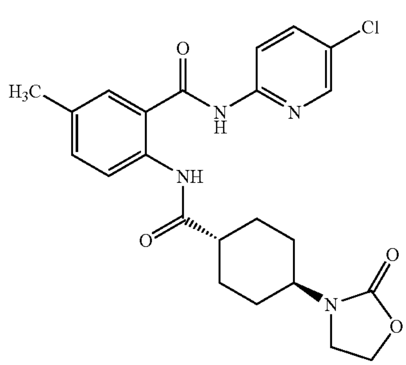 | APCI-MS M/Z: 457/459 [M + H]+ |

| Ex. No. | Structure | Physicochemical Properties |
|---|---|---|
| 26 | 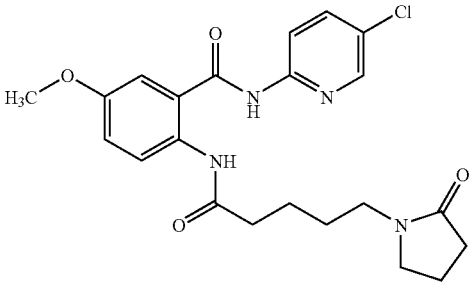 | APCI-MS M/Z: 455/457 [M + H]$^+$ |
| 27 | 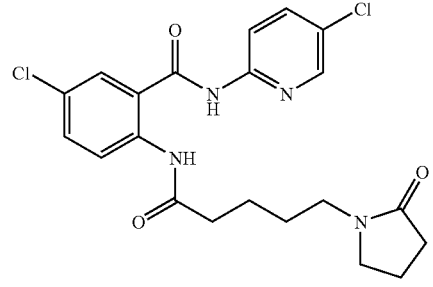 | APCI-MS M/Z: 449/451 [M + H]$^+$ |
| 28 | 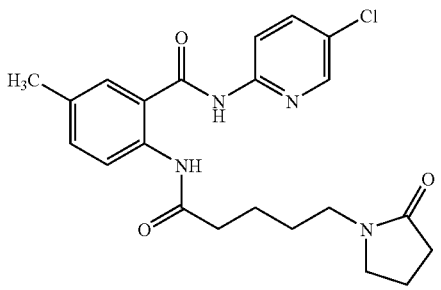 | APCI-MS M/Z: 429/431 [M + H]$^+$ |
| 29 | 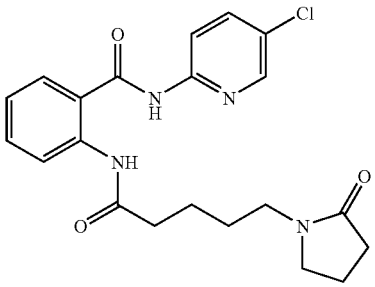 | APCI-MS M/Z: 415/417 [M + H]$^+$ |
| 30 | 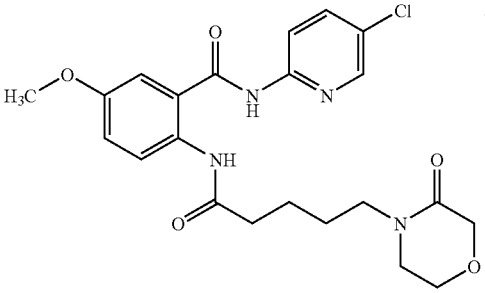 | APCI-MS M/Z: 461/463 [M + H]$^+$ |

-continued

| Ex. No. | Structure | Physicochemical Properties |
|---|---|---|
| 31 | 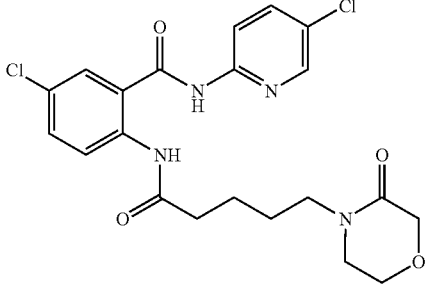 | APCI-MS M/Z: 465/467 [M + H]⁺ |
| 32 | 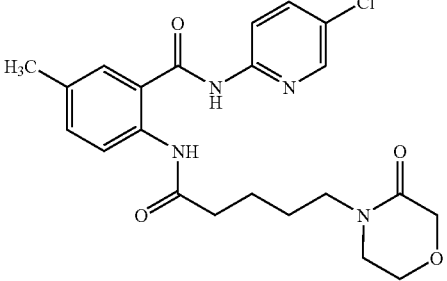 | APCI-MS M/Z: 445/447 [M + H]⁺ |
| 33 | 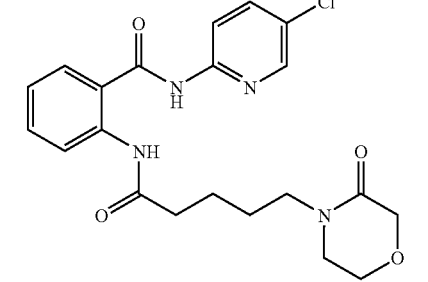 | APCI-MS M/Z: 431/433 [M + H]⁺ |

Example 34

N-(5-Chloropyridin-2-yl)-3-({[trans-4-(2-oxopyrrolidin-1-yl)cyclohexyl]carbonyl}amino)-2-naphthamide

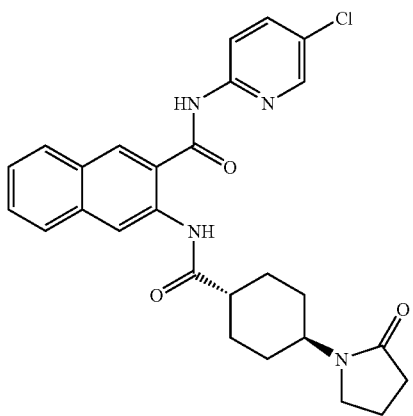

(1) A suspension of 2H-naphth[2,3-d][1,3]oxazine-2,4(1H)-dione (216 mg) and 2-amino-5-chloropyridine (202 mg) in xylene (5 ml) is stirred at 150° C. for 13 hours, and thereto added 4-dimethylaminopyridine (14.4 mg) and the mixture is stirred at 150° C. for another 3 hours. The reaction solution is concentrated under reduced pressure and the resulting residue is suspended in ethyl acetate, and filtered to remove insoluble materials. The filtrate is concentrated under reduced pressure, and the residue is purified by silica gel column chromatography (eluent: n-hexane/ethyl acetate=2/1) to give 3-amino-N-(5-chloropyridin-2-yl)-2-naphthamide (24 mg).

APCI-MS m/z:298/300[M+H]⁺

(2) Trans-4-(2-oxopyrrolidin-1-yl)cyclohexane-carboxylic acid (40 mg) obtained in Reference Example 2 is dissolved in chloroform (3 ml), and thereto are added thionyl chloride (15 μl) and N,N-dimethylformamide (1 drop) followed by stirring at room temperature for 15 hours. To the reaction solution are added 3-amino-N-(5-chloropyridin-2-yl)-2-naphthamide (31 mg) obtained in Example 34(1) and pyridine (1 ml), and the mixture is stirred at room temperature for 12 hours. After adding trans-4-(2-oxopyrrolidin-1-yl)cyclohexanecarboxylic acid (43 mg), 1-ethyl-3-(3-dimethylaminopropyl)carbodiimide hydrochloride (42 mg) and 4-(dimethylamino)pyridine (56 mg), the mixture is stirred at room temperature for another 12 hours. To the reaction solution is poured saturated aqueous sodium hydrogen carbonate solution, and the mixture is extracted with chloroform. The extract is dried over sodium sulfate and evaporated to remove the solvent under reduced pressure. The resulting residue is purified by NH-silica gel column chromatography (eluent: n-hexane/ethyl acetate=1/1, then 1/4) to give title compound (36 mg).

APCI-MS M/Z: 491/493[M+H]$^+$

Example 35

N-(5-Chloropyridin-2-yl)-3-({[trans-4-(3-oxomorpholin-4-yl)cyclohexyl]carbonyl}amino)pyridine-2-carboxamide

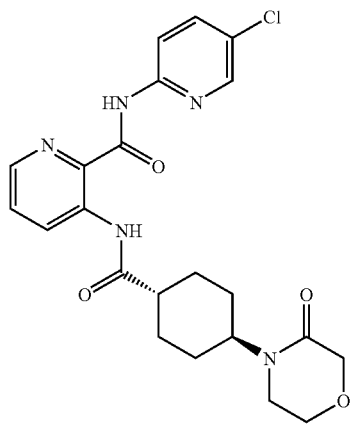

Trans-4-(3-oxomorpholin-4-yl)cyclohexanecarboxylic acid (120 mg) obtained in Reference Example 4 is dissolved in chloroform (3 ml), and thereto are added 1M thionyl chloride-chloroform solution (540 µl) and N,N-dimethylformamide (1 drop), followed by stirring at room temperature for 7 hours. To the reaction solution are added 3-amino-N-(5-chloropyridin-2-yl)pyridine-2-carboxamide (99 mg) and pyridine (1 ml), and the mixture is stirred at room temperature overnight. After poring saturated aqueous sodium hydrogen carbonate solution to the reaction solution, the mixture is extracted with chloroform. The organic layer is concentrated under reduced pressure, and the resulting residue is purified by NM-silica gel column chromatography (eluent: n-hexane/ethyl acetate=1/1, then ethyl acetate) to give the title compound (94 mg). APCI-MS M/Z: 458/460 [M+H]$^+$

Examples 36-44

The corresponding amino compounds and carboxylic acids are treated in a similar manner to Example 35 to give the following compounds.

| Ex. No. | Structure | Physicochemical Properties |
|---|---|---|
| 36 | ![structure] | APCI-MS M/Z: 472/474 [M + H]$^+$ |

-continued

| Ex. No. | Structure | Physicochemical Properties |
| --- | --- | --- |
| 37 | 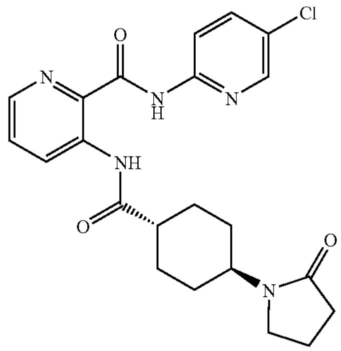 | APCI-MS<br>M/Z: 442/444 [M + H]+ |
| 38 | 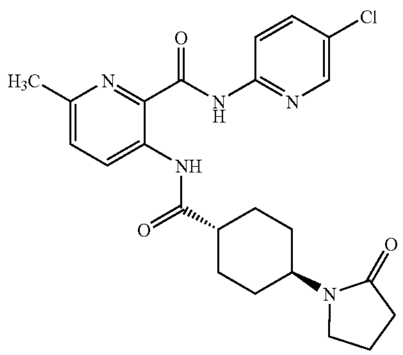 | APCI-MS<br>M/Z: 456/458 [M + H]+ |
| 39 | 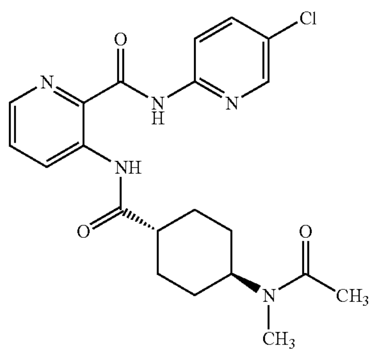 | APCI-MS<br>M/Z: 430/432 [M + H]+ |
| 40 | 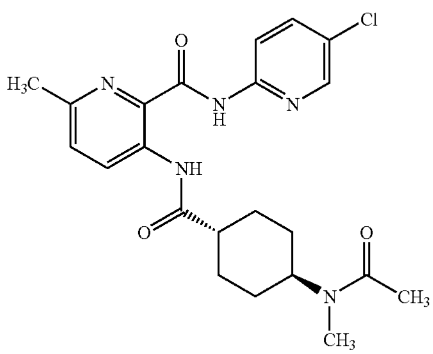 | APCI-MS<br>M/Z: 444/446 [M + H]+ |

-continued

| Ex. No. | Structure | Physicochemical Properties |
|---|---|---|
| 41 | 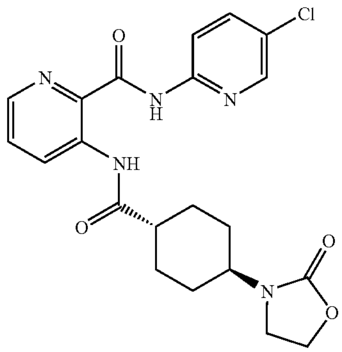 | APCI-MS M/Z: 444/446 [M + H]+ |
| 42 | 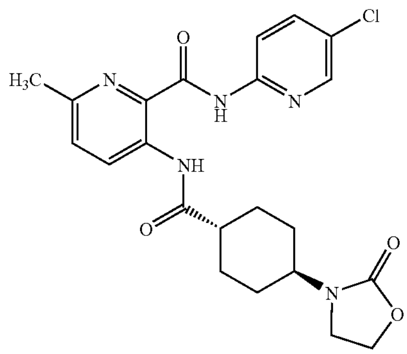 | APCI-MS M/Z: 458/460 [M + H]+ |
| 43 | 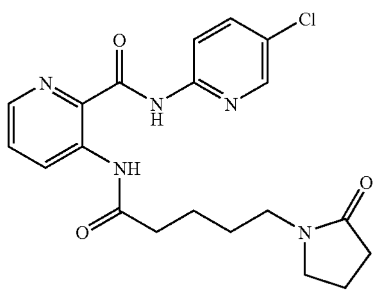 | APCI-MS M/Z: 459/461 [M + H]+ |
| 44 | 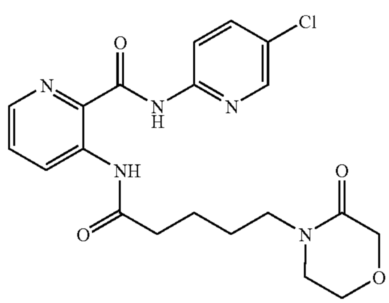 | APCI-MS M/Z: 432/434 [M + H]+ |

Example 45

Methyl 3-({[trans-4-(3-oxomorpholin-4-yl)-cyclohexyl]carbonyl}amino)thiophene-2-carboxylate

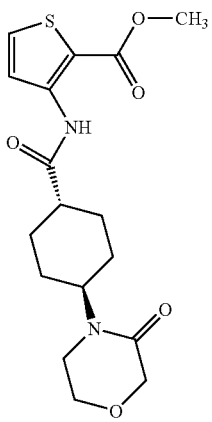

Trans-4-(3-oxomorpholin-4-yl)cyclohexanecarboxylic acid (1193 mg) obtained in Reference Example 4 is dissolved in thionyl chloride (10 ml), and the mixture is stirred at room temperature for 18 hours. The reaction solution is concentrated under reduced pressure. The residue is subjected to azeotropic distillation with toluene and dissolved in chloroform (7 ml). Methyl 3-aminothiophene-2-carboxylate (79 mg) is dissolved in pyridine (3 ml), and thereto is added the chloroform solution (1 ml) prepared above under ice-cooling. The reaction solution is warmed to room temperature and stirred for 21 hours. To the reaction solution is poured saturated aqueous sodium hydrogen carbonate solution, and the mixture is extracted with chloroform. The organic layer is successively washed with water and saturated brine, dried over sodium sulfate, and evaporated to remove the solvent under reduced pressure. The resulting residue is purified by NH-silica gel column chromatography (eluent: n-hexane/ethyl acetate=1/1) to give the title compound (188 mg). APCI-MS M/Z: 367[M+H]$^+$

Examples 46-68

The corresponding amino compounds and carboxylic acids are treated in a similar manner to Example 45 to give the following compounds.

| Ex. No. | Structure | Physicochemical Properties |
|---|---|---|
| 46 | (structure) | APCI-MS M/Z: 423 [M + H]$^+$ |
| 47 | (structure) | APCI-MS M/Z: 443 [M + H]$^+$ |

-continued
| Ex. No. | Structure | Physicochemical Properties |
|---|---|---|
| 48 | 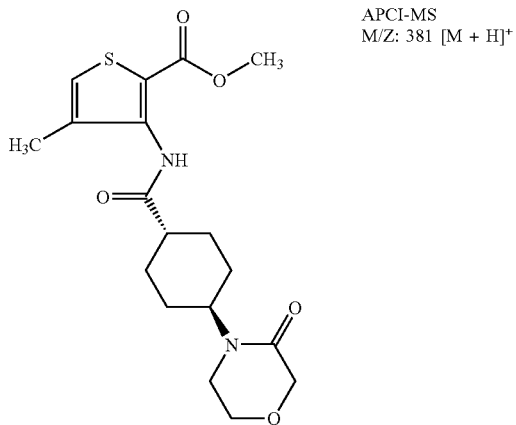 | APCI-MS M/Z: 381 [M + H]+ |
| 49 | 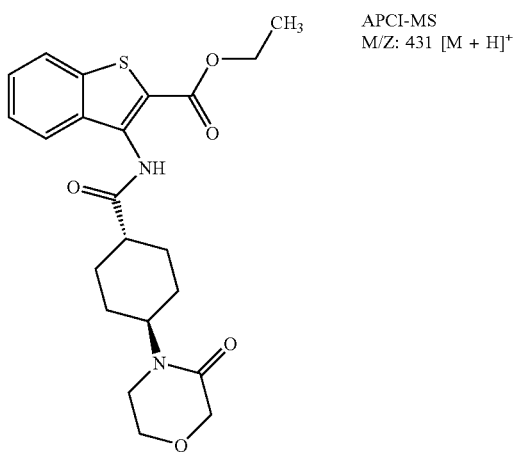 | APCI-MS M/Z: 431 [M + H]+ |
| 50 | 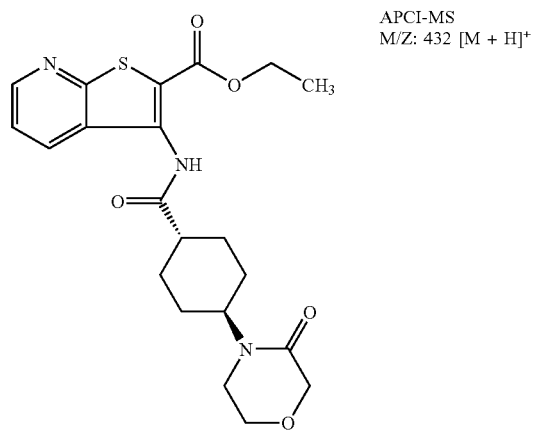 | APCI-MS M/Z: 432 [M + H]+ |

-continued
| Ex. No. | Structure | Physicochemical Properties |
|---|---|---|
| 51 | 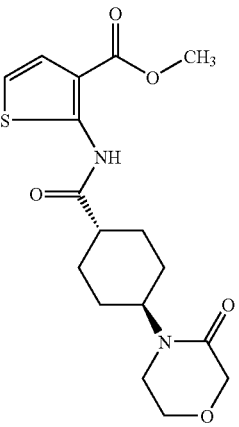 | APCI-MS<br>M/Z: 367 [M + H]+ |
| 52 | 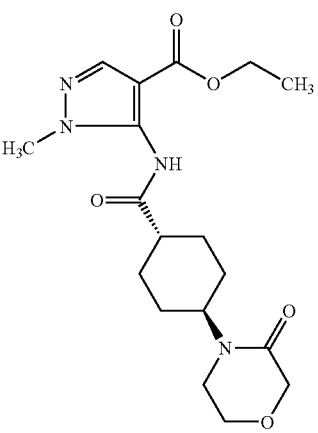 | APCI-MS<br>M/Z: 379 [M + H]+ |
| 53 | 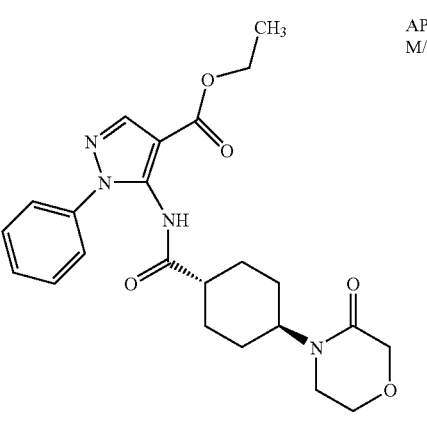 | APCI-MS<br>M/Z: 441 [M + H]+ |

-continued

| Ex. No. | Structure | Physicochemical Properties |
|---------|-----------|----------------------------|
| 54 | 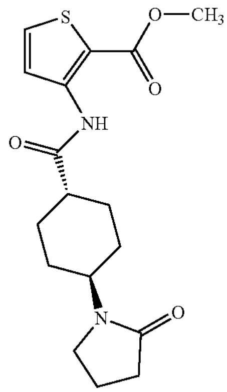 | APCI-MS<br>M/Z: 351 [M + H]+ |
| 55 | 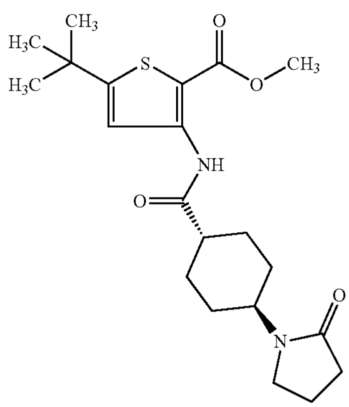 | APCI-MS<br>M/Z: 407 [M + H]+ |
| 56 | 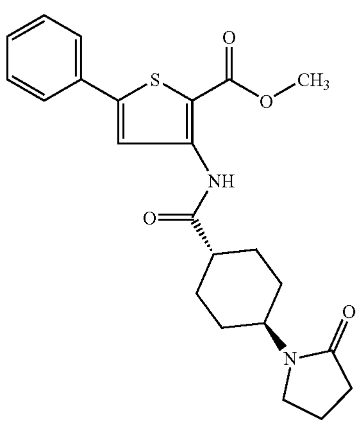 | APCI-MS<br>M/Z: 427 [M + H]+ |

-continued

| Ex. No. | Structure | Physicochemical Properties |
|---|---|---|
| 57 | 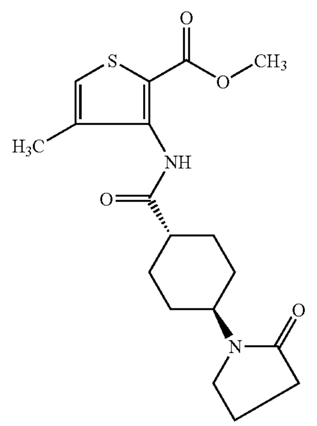 | APCI-MS M/Z: 365 [M + H]+ |
| 58 | 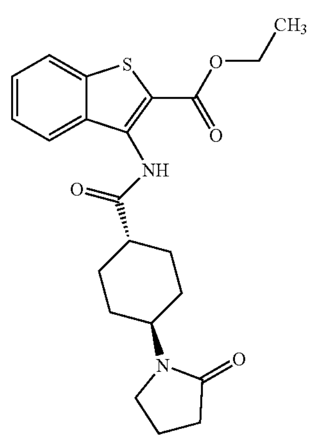 | APCI-MS M/Z: 415 [M + H]+ |
| 59 | 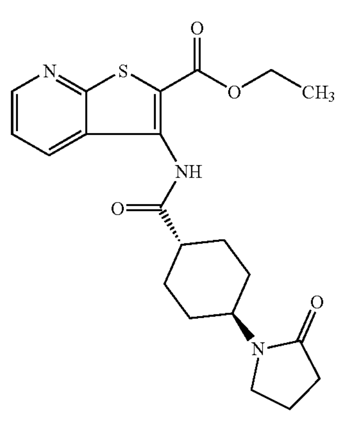 | APCI-MS M/Z: 416 [M + H]+ |

-continued
| Ex. No. | Structure | Physicochemical Properties |
|---|---|---|
| 60 | 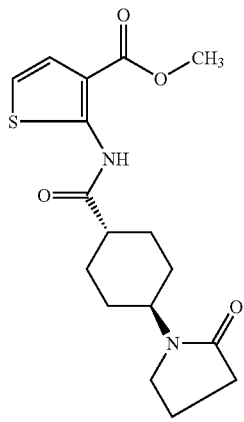 | APCI-MS M/Z: 351 [M + H]$^+$ |
| 61 | 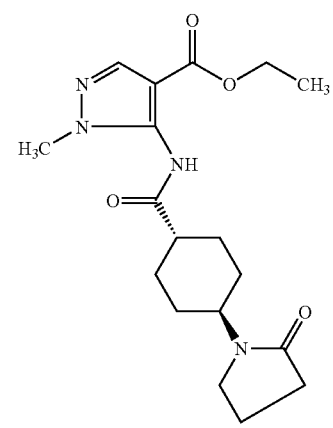 | APCI-MS M/Z: 363 [M + H]$^+$ |
| 62 | 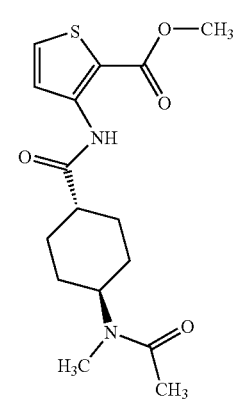 | APCI-MS M/Z: 339 [M + H]$^+$ |

-continued

| Ex. No. | Structure | Physicochemical Properties |
|---|---|---|
| 63 | 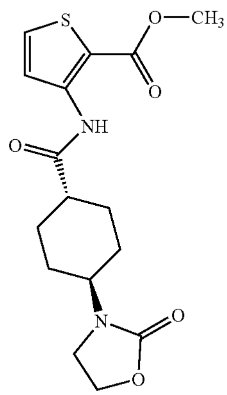 | APCI-MS M/Z: 353 [M + H]+ |
| 64 | 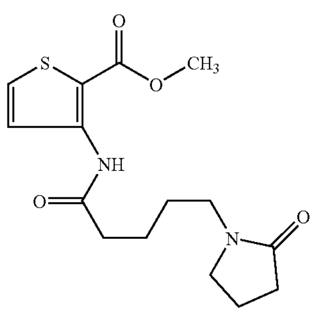 | APCI-MS M/Z: 325 [M + H]+ |
| 65 | 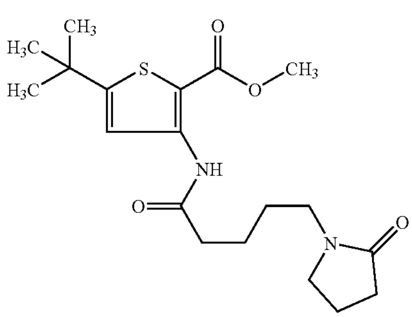 | APCI-MS M/Z: 381 [M + H]+ |

| Ex. No. | Structure | Physicochemical Properties |
|---|---|---|
| 66 | 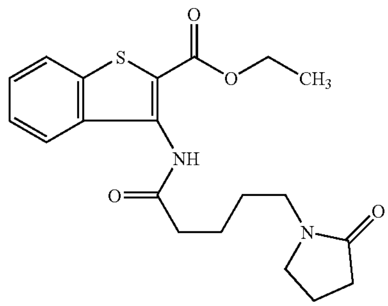 | APCI-MS M/Z: 389 [M + H]+ |
| 67 | 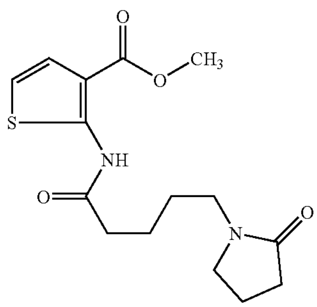 | APCI-MS M/Z: 325 [M + H]+ |
| 68 | 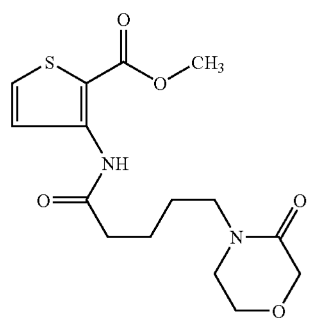 | APCI-MS M/Z: 341 [M + H]+ |

Example 69
N-(5-Chloropyridin-2-yl)-3-({[trans-4-(3-oxomorpholin-4-yl)cyclohexyl]carbonyl}amino)thiophene-2-carboxamide

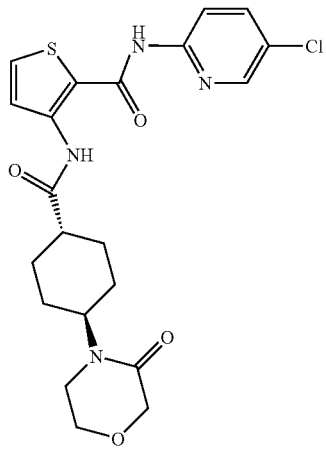

2-Amino-5-chloropyridine (179 mg) is dissolved in chloroform (5 ml), and there to is added dropwise 0.98 M trimethyl aluminum-hexane solution (1.42 ml) under ice-cooling. The reaction solution is stirred at room temperature for 0.5 hours, and thereto is added methyl 3-({[trans-4-(3-oxomorpholin-4-yl)cyclohexyl]carbonyl}amino)-thiophene-2-carboxylate (170 mg), and the mixture is heated to reflux for 18 hours. After allowing to cool, to the reaction mixture is added 10% hydrochloric acid (4 ml), and the mixture is extracted with chloroform. The organic layer is washed successively with water and saturated brine, dried over sodium sulfate, and evaporated to remove the solvent under reduced pressure. The resulting residue is purified by NH-silica gel column chromatography (eluent: chloroform) to give the title compound (172 mg). APCI-MS M/Z: 463/465[M+H]+

Examples 70-92

The corresponding esters are treated in a similar manner to Example 69 to give the following compounds.

| Ex. No. | Structure | Physicochemical Properties |
|---|---|---|
| 70 | 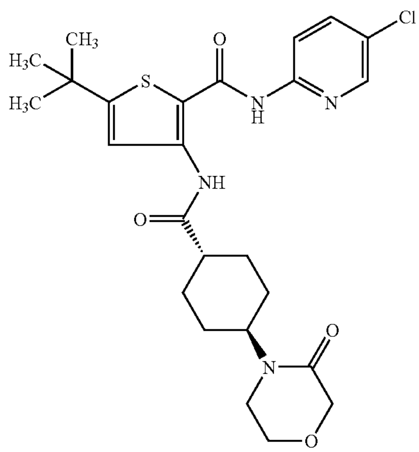 | APCI-MS M/Z: 519/521 [M + H]+ |
| 71 | 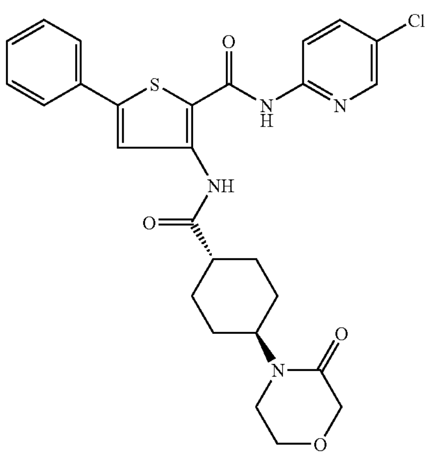 | APCI-MS M/Z: 539/541 [M + H]+ |
| 72 | 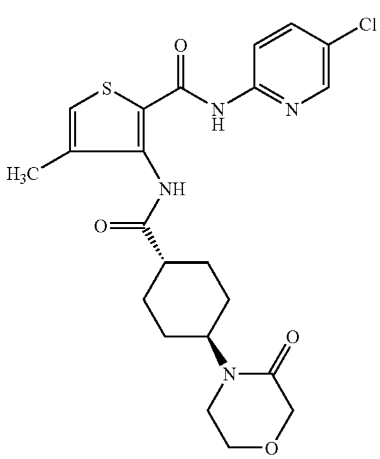 | APCI-MS M/Z: 447/449 [M + H]+ |

-continued

| Ex. No. | Structure | Physicochemical Properties |
|---|---|---|
| 73 | 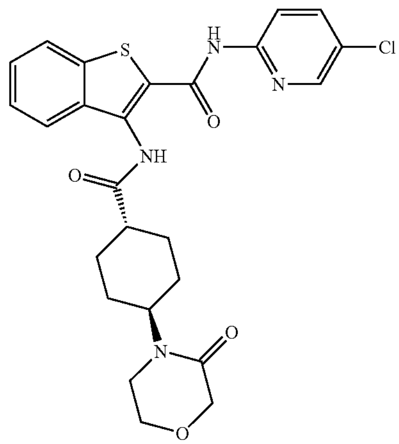 | APCI-MS M/Z: 513/515 [M + H]+ |
| 74 | 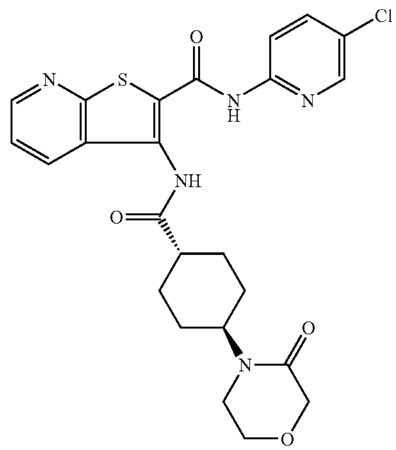 | APCI-MS M/Z: 514/516 [M + H]+ |
| 75 | 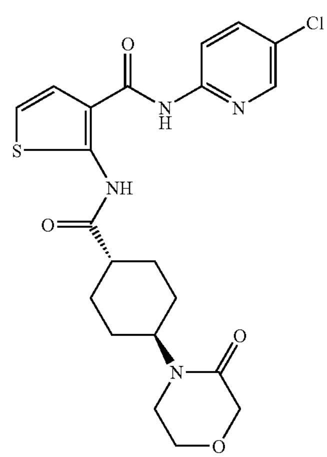 | APCI-MS M/Z: 463/465 [M + H]+ |

| Ex. No. | Structure | Physicochemical Properties |
|---|---|---|
| 76 | 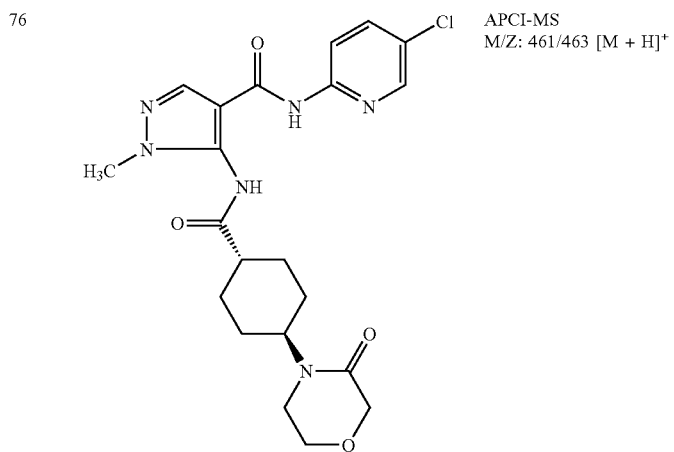 | APCI-MS M/Z: 461/463 [M + H]+ |
| 77 | 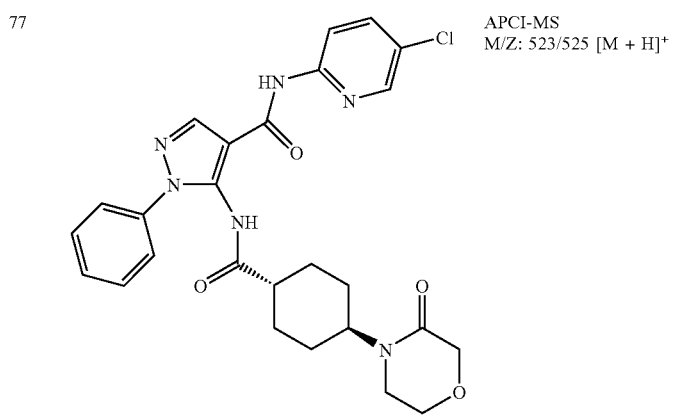 | APCI-MS M/Z: 523/525 [M + H]+ |
| 78 | 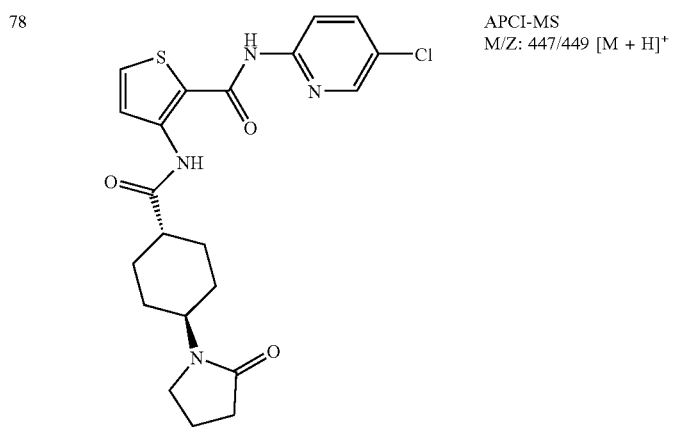 | APCI-MS M/Z: 447/449 [M + H]+ |

| Ex. No. | Structure | Physicochemical Properties |
|---|---|---|
| 79 | 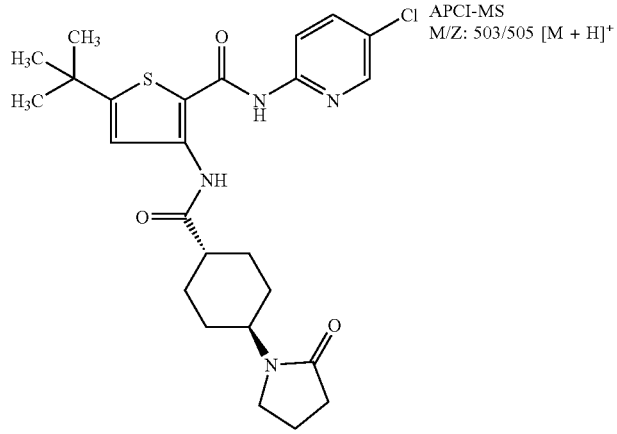 | APCI-MS M/Z: 503/505 [M + H]+ |
| 80 | 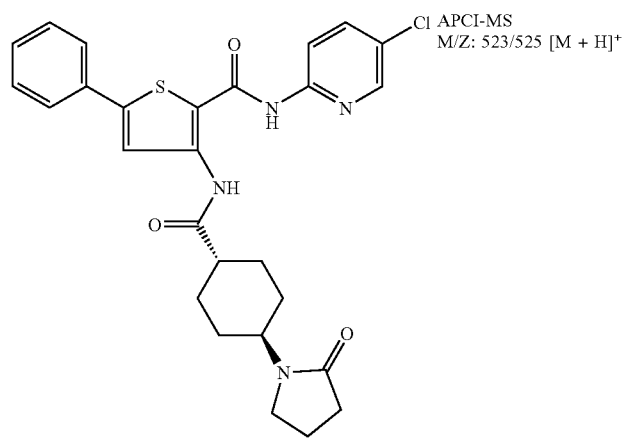 | APCI-MS M/Z: 523/525 [M + H]+ |
| 81 | 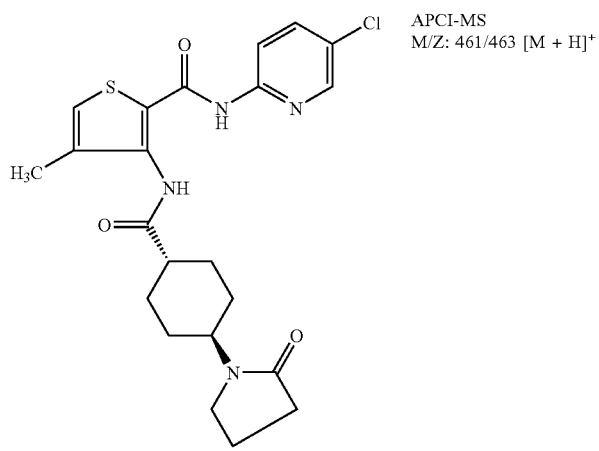 | APCI-MS M/Z: 461/463 [M + H]+ |

-continued

| Ex. No. | Structure | Physicochemical Properties |
|---|---|---|
| 82 | 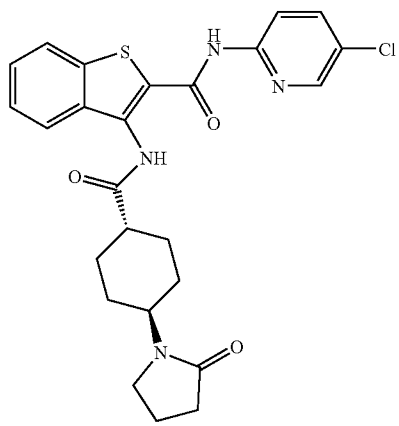 | APCI-MS M/Z: 497/499 [M + H]+ |
| 83 | 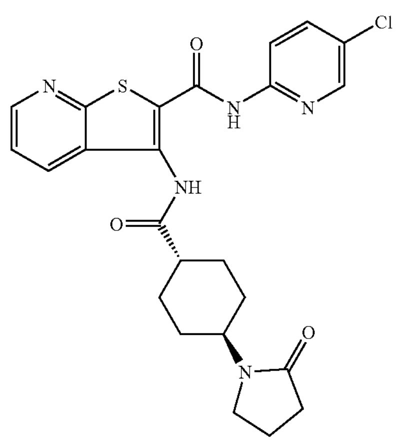 | APCI-MS M/Z: 498/500 [M + H]+ |
| 84 | 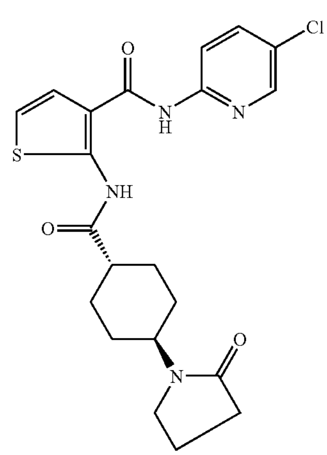 | APCI-MS M/Z: 447/449 [M + H]+ |

| Ex. No. | Structure | Physicochemical Properties |
|---|---|---|
| 85 | 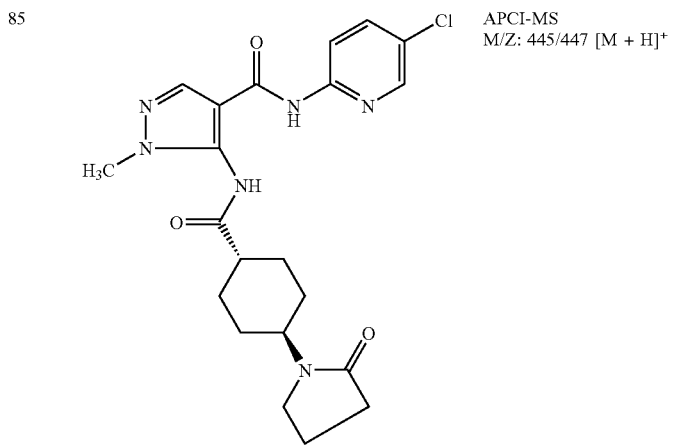 | APCI-MS M/Z: 445/447 [M + H]+ |
| 86 | 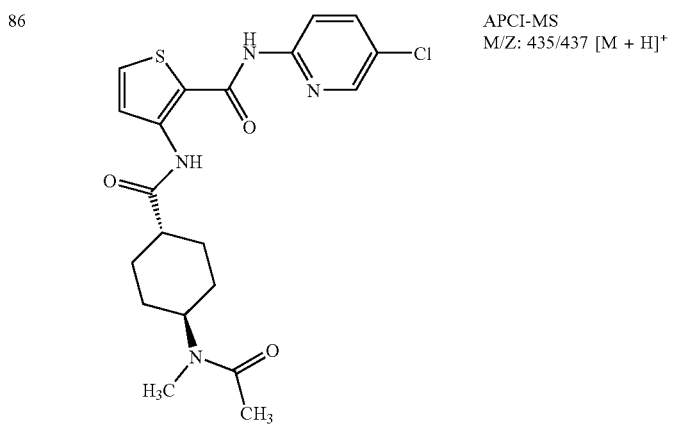 | APCI-MS M/Z: 435/437 [M + H]+ |
| 87 | 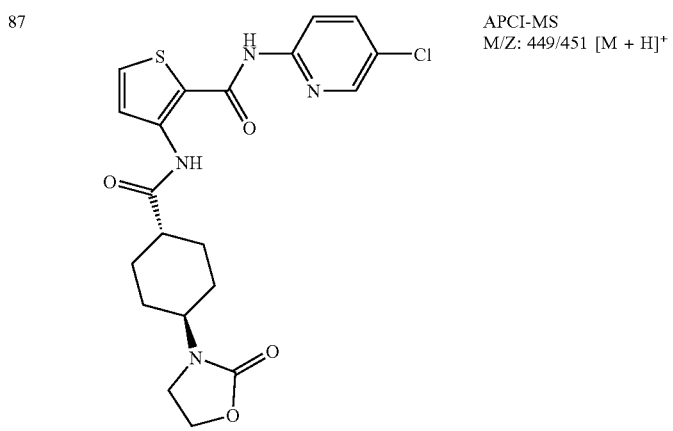 | APCI-MS M/Z: 449/451 [M + H]+ |

-continued

| Ex. No. | Structure | Physicochemical Properties |
| --- | --- | --- |
| 88 | 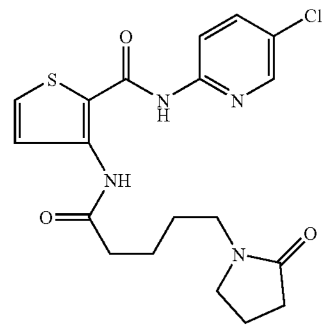 | APCI-MS M/Z: 421/423 [M + H]+ |
| 89 | 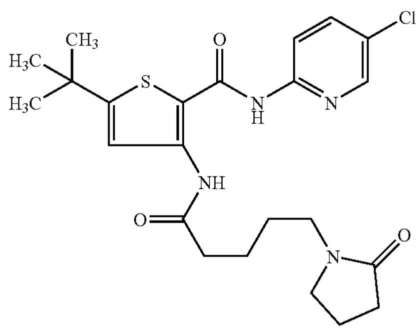 | APCI-MS M/Z: 477/479 [M + H]+ |
| 90 | 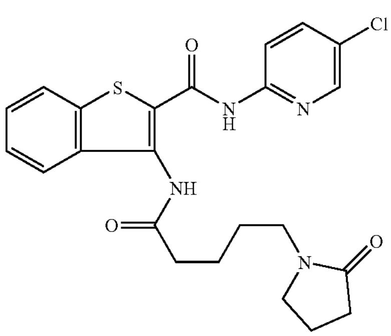 | APCI-MS M/Z: 471/473 [M + H]+ |
| 91 | 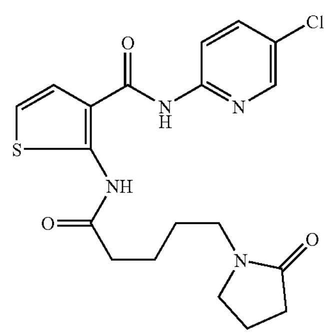 | APCI-MS M/Z: 421/423 [M + H]+ |

| Ex. No. | Structure | Physicochemical Properties |
|---|---|---|
| 92 | 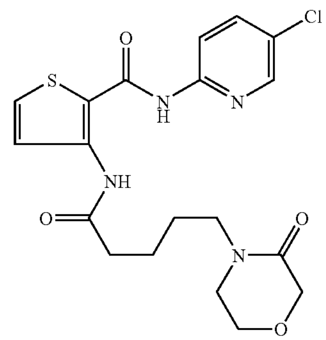 | APCI-MS M/Z: 437/439 [M + H]+ |

Examples 93-105

The corresponding amino compounds and carboxylic acids obtained in Reference Examples 8-11 are treated in a similar manner to Example 1 to give the following compounds.

| Ex. No. | Structure | Physicochemical Properties |
|---|---|---|
| 93 | 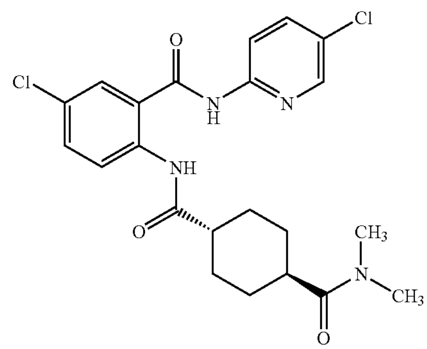 | APCI-MS M/Z: 463/465 [M + H]+ |
| 94 | 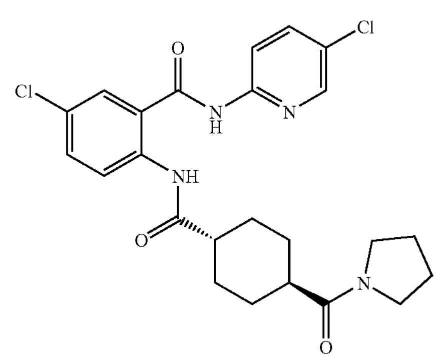 | APCI-MS M/Z: 489/491 [M + H]+ |

-continued

| Ex. No. | Structure | Physicochemical Properties |
|---|---|---|
| 95 | 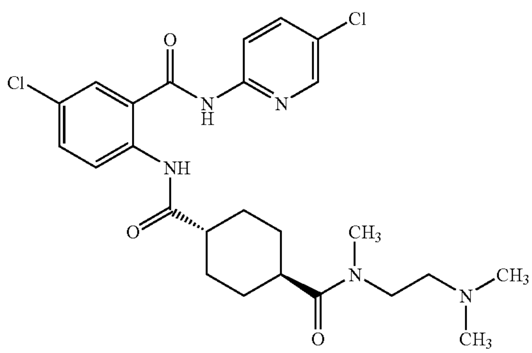 | APCI-MS M/Z: 520/522 [M + H]+ |
| 96 | 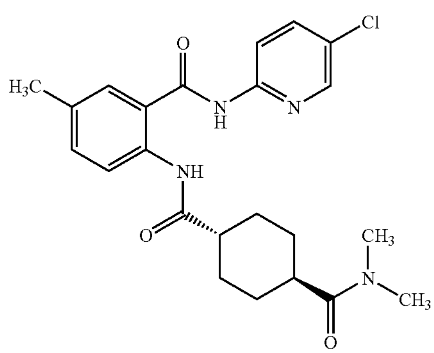 | APCI-MS M/Z: 443/445 [M + H]+ |
| 97 | 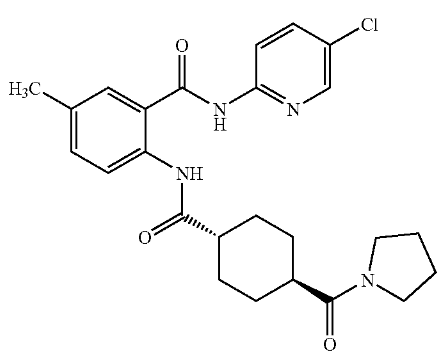 | APCI-MS M/Z: 469/471 [M + H]+ |
| 98 | 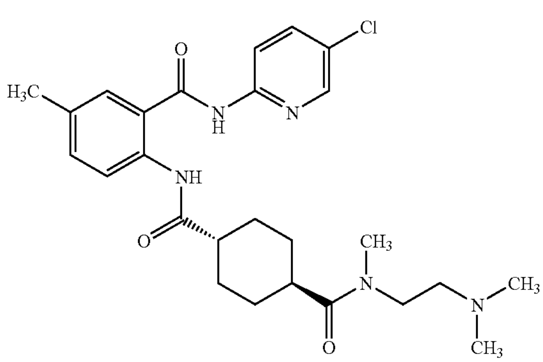 | APCI-MS M/Z: 500/502 [M + H]+ |

-continued

| Ex. No. | Structure | Physicochemical Properties |
|---|---|---|
| 99 | 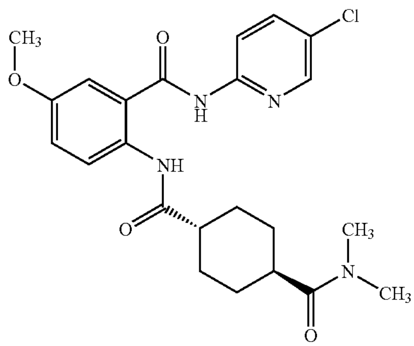 | APCI-MS M/Z: 459/461 [M + H]+ |
| 100 | 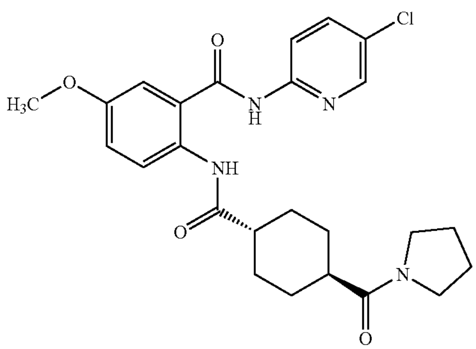 | APCI-MS M/Z: 485/487 [M + H]+ |
| 101 | 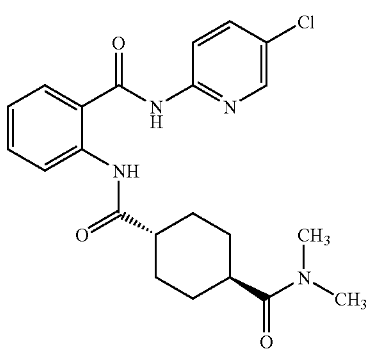 | APCI-MS M/Z: 429/431 [M + H]+ |
| 102 | 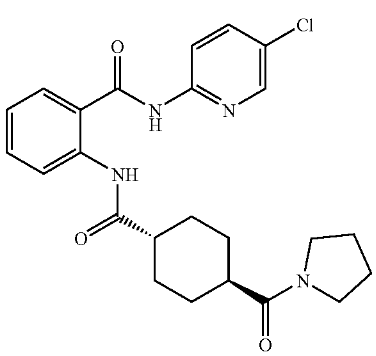 | APCI-MS M/Z: 455/457 [M + H]+ |

-continued

| Ex. No. | Structure | Physicochemical Properties |
|---|---|---|
| 103 | 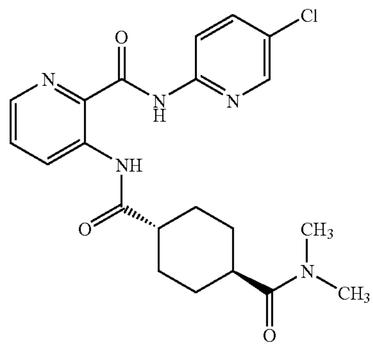 | APCI-MS M/Z: 430/432 [M + H]+ |
| 104 | 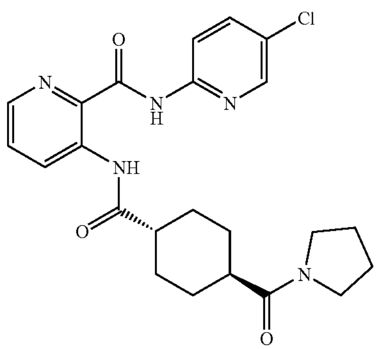 | APCI-MS M/Z: 456/458 [M + H]+ |
| 105 | 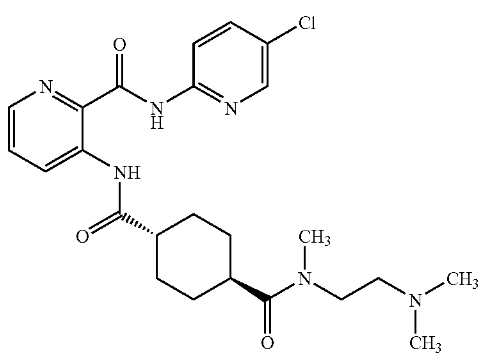 | APCI-MS M/Z: 487/489 [M + H]+ |

Reference Example 1

Methyl trans-4-[(t-butoxycarbonyl)-amino]cyclohexanecarboxylate

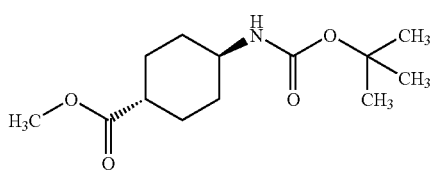

(1) Thionyl chloride (254 ml) is added dropwise to methanol (1500 ml) under cooling to −30° C. over a period of about an hour. After the addition, the reaction mixture is stirred at room temperature for 0.5 hours, and thereto is added trans-cyclohexane-1,4-dicarboxylic acid (500.0 g), and the mixture is stirred at room temperature for 17 hours. The reaction solution is concentrated under reduced pressure. The residue is diluted with chloroform, and washed with saturated aqueous sodium hydrogen carbonate solution and saturated brine. The organic layer is dried over sodium sulfate and evaporated to remove solvent under reduced pressure. The resulting residue is crystallized from n-hexane, collected by filtration and dried to give dimethyl trans-cyclohexane-1,4-dicarboxylate (545.0 g).

APCI-MS M/Z: 201[M+H]+

(2) Dimethyl trans-cyclohexane-1,4-dicarboxylate (150.0 g) obtained in (1) above is dissolved in tetrahydrofuran (1500 ml), and to the solution is added dropwise a mixed solution of 28% sodium methoxide/methanol (149 g) and water (13.2 g) under ice-cooling. The reaction solution is warmed to room temperature, stirred for 3.5 hours, and thereto is poured n-hexane (1500 ml) and the mixture is filtered to collect the precipitates. The resulting solid is added to a mixture of conc. hydrochloric acid (50 ml), water (450 ml) and chloroform (1000 ml) under ice-cooling, and the mixture is stirred at room temperature for 20 minutes. The chloroform layer is separated and the aqueous layer is extracted with chloroform. The organic layers are combined, dried over sodium sulfate and evaporated to remove the solvent under reduced pressure. The resulting residue is crystallized from n-hexane, collected by filtration and dried to give trans-4-(methoxycarbonyl)cyclohexanecarboxylic acid (106.0 g).

ESI-MS M/Z:185[M−H]⁻

(3) Trans-4-(methoxycarbonyl)cyclohexanecarboxylic acid (100.0 g) obtained in (2) above is dissolved in t-butanol (1000 ml), and thereto are added diphenylphosphoryl azide (155 g) and triethylamine (78.6 ml). The mixture is heated at about 60° C. for an hour and further heated under reflux for additional 17 hours. After allowing to cool, to the reaction solution is added ice-water, and the mixture is extracted with ethyl acetate. The organic layer is washed with saturated aqueous sodium hydrogen carbonate solution and saturated brine, dried over sodium sulfate and evaporated to remove the solvent under reduced pressure. The resulting residue is dissolved in methanol (250 ml), and thereto is added water (750 ml) and the mixture is stirred under ice-cooling. After 0.5 hours, the precipitates are collected by filtration, washed with water/methanol (3:1, 1000 ml) and n-hexane successively and dried to give the title compound (117.0 g).

APCI-MS M/Z: 275[M+H]⁺

Reference Example 2

Trans-4-(2-oxopyrrolidin-1-yl)-cyclohexanecarboxylic acid

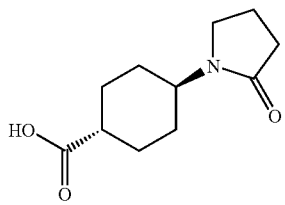

(1) Methyl trans-4-[(t-butoxycarbonyl)amino]-cyclohexanecarboxylate (234.0 g) obtained in Reference Example 1 is dissolved in dioxane (500 ml), and thereto is added 4 N hydrogen chloride/dioxane (500 ml), and the mixture is stirred at room temperature for 19 hours. The reaction solution is concentrated under reduced pressure, and the resulting residue is suspended in diethyl ether. The precipitates are collected by filtration to give methyl trans-4-aminocyclohexanecarboxylate hydrochloride (121.9 g)

APCI-MS M/Z:158[M+H]⁺

(2) Methyl trans-4-aminocyclohexanecarboxylate hydrochloride (45.31 g) obtained in (1) above is suspended in dichloromethane (1000 ml), and thereto is added 4-chlorobutyryl chloride (31.5 ml) under ice-cooling, followed by dropwise addition of a solution of triethylamine (81.5 ml) in dichloromethane (80 ml). The reaction solution is warmed to room temperature, stirred for 3 hours and concentrated under reduced pressure. To the resulting residue are poured ethyl acetate and 5% hydrochloric acid, and the organic layer is separated, washed with saturated aqueous sodium hydrogen carbonate solution and saturated brine. The organic layer is dried over sodium sulfate and treated with activated carbon, and the filtrate is concentrated under reduced pressure. The resulting residue is suspended in diisopropyl ether. The precipitates are collected by filtration and dried to give methyl trans-4-[(4-chlorobutanoyl)amino]cyclohexane-carboxylate (38.81 g). APCI-MS M/Z:262/264[M+H]⁺

(3) Sixty % sodium hydride in oil (9.60 g) is suspended in N,N-dimethylacetamide (500 ml), and to the mixture is added methyl trans-4-[(4-chloro-butanoyl)amino)]cyclohexanecarboxylate (52.32 g) obtained in (2) above in small portions under ice-cooling. The reaction solution is warmed to room temperature, stirred for 24 hours, and thereto are poured saturated aqueous ammonium chloride solution and ice-water. The reaction mixture is extracted with chloroform. The organic layer is washed with saturated brine, dried over magnesium sulfate and evaporated to remove the solvent under reduced pressure. The resulting residue is purified by silica gel column chromatography (eluent: ethyl acetate) and the residue is suspended in n-hexane/diisopropyl ether. The resulting crystals are collected by filtration and dried to give methyl trans-4-(2-oxopyrrolidin-1-yl)cyclohexanecarboxylate (39.20 g). APCI-MS M/Z:226[M+H]⁺

(4) Methyl trans-4-(2-oxopyrrolidin-1-yl)cyclohexanecarboxylate (39.15 g) obtained in (3) above is dissolved in methanol (400 ml), and thereto is added 2 N aqueous sodium hydroxide solution (174 ml). The mixture is stirred at room temperature for 3 hours. The reaction solution is adjusted to pH 1-2 with 10% hydrochloric acid under ice-cooling, and saturated with sodium chloride, followed by extraction with chloroform. The organic layer is dried over sodium sulfate, and then evaporated to remove the solvent under reduced pressure. The resulting residue is suspended in a small amount of ethyl acetate, and diisopropyl ether is poured thereto. The resulting crystals are collected by filtration, washed with diisopropyl ether several times and dried to give the title compound (35.94 g). ESI-MS M/Z:210[M−H]⁻

Reference Example 3

Trans-4-[acetyl(methyl)amino]-cyclohexanecarboxylic acid

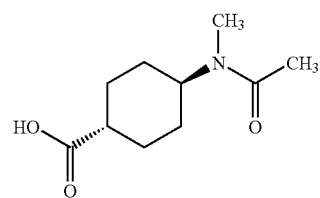

(1) Methyl trans-4-[(t-butoxycarbonyl)amino]-cyclohexanecarboxylate (30.00 g) obtained in Reference Example 1 is dissolved in N,N-dimethylformamide (150 ml) and thereto is added 60% sodium hydride in oil (5.60 g) under ice-cooling. After stirring for 0.5 hours under the same cooling conditions, methyl iodide (14.5 ml) and methanol (0.15 ml) are added to the reaction solution successively. The reaction solution is warmed to room temperature and stirred for 4 hours. Under ice-cooling, to the reaction solution are poured saturated aqueous ammonium chloride solution and ice-water, and the mixture is extracted with ethyl acetate. The organic layer is washed with water and saturated brine successively, dried over sodium sulfate and evaporated to remove the solvent under reduced pressure. The resulting residue is purified by silica gel column chromatography (eluent: n-hexane/ethyl acetate=10/1, followed by 7/1) to give methyl trans-4-[(t-butoxycarbonyl)(methyl)amino)cyclohexanecarboxylate (26.33 g). APCI-MS M/Z: 272[M+H]+

(2) Methyl trans-4-[(t-butoxycarbonyl)(methyl)amino]-cyclohexanecarboxylate (26.32 g) obtained in (1) above is dissolved in dioxane (100 ml), and thereto is added 4 N hydrogen chloride/dioxane solution (100 ml). The reaction solution is stirred at room temperature for 4 hours, and to the solution is poured diisopropyl ether (500 ml). The precipitates are collected by filtration, washed with diisopropyl ether and dried to give methyl trans-4-(methylamino)cyclohexanecarboxylate hydrochloride (19.01 g).

APCI-MS M/Z:172[M+H]+

(3) Methyl trans-4-(methylamino)cyclohexane-carboxylate hydrochloride (18.93 g) obtained in (2) above is suspended in dichloromethane (400 ml), and to the solution is added acetyl chloride (8.42 ml) under ice-cooling, followed by dropwise addition of a solution of triethylamine (38.1 ml) in dichloromethane (40 ml). The reaction solution is warmed to room temperature and stirred for 2 hours. After adding 5% hydrochloric acid, the mixture is extracted with dichloromethane. The organic layer is washed with saturated brine, dried over sodium sulfate and evaporated to remove the solvent under reduced pressure. The resulting residue is purified by NH-silica gel column chromatography (eluent: ethyl acetate) to give methyl trans-4-[acetyl(methyl)amino]cyclohexanecarboxylate (19.05 g). APCI-MS M/Z:214[M+H]+

(4) Methyl trans-4-[acetyl(methyl)amino]cyclohexane-carboxylate (19.00 g) obtained in (3) above is dissolved in methanol (200 ml), and thereto is added 2 N aqueous sodium hydroxide solution (60 ml). The mixture is then stirred at room temperature for 3 hours. Under ice-cooling, the reaction solution is adjusted to pH 1-2 by pouring 10% hydrochloric acid, saturated with sodium chloride, and then extracted with chloroform. The organic layer is dried over sodium sulfate, and evaporated to remove the solvent under reduced pressure. The resulting residue is suspended in a small amount of ethyl acetate, and to the mixture is poured diisopropyl ether. The crystals are collected by filtration, washed with diisopropyl ether several times and dried to give the title compound (16.31 g).

ESI-MS M/Z:198[M−H]−

Reference Example 4

Trans-4-(3-oxomorpholin-4-yl)-cyclohexanecarboxylic acid

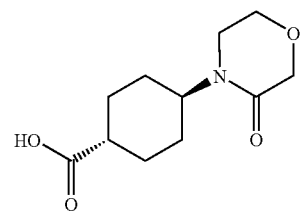

(1) Sixty % sodium hydride in oil (6.80 g) is suspended in N,N-dimethylacetamide (80 ml) and a solution of 2-(benzyloxy)ethanol (12.9 g) in N,N-dimethylacetamide (50 ml) is added dropwise to the mixture over 10 minutes under ice-cooling. After stirring at room temperature for 15 minutes, the reaction solution is cooled with ice, and thereto is added chloroacetic acid (8.13 g) in small portions. The mixture is then stirred at room temperature for 11 hours. The reaction solution is concentrated under reduced pressure, and to the resulting residue is added aqueous sodium hydrogen carbonate solution and the mixture is washed with diethyl ether. The aqueous layer is acidified with conc. hydrochloric acid, and then extracted with ethyl acetate. The organic layer is washed with saturated brine, dried over sodium sulfate and evaporated to remove solvent under reduced pressure to give [2-(benzyloxy)ethoxy]acetic acid (18.24 g).

ESI-MS M/Z:209[M−H]−

(2) [(2-Benzyloxy)ethoxy]acetic acid (6.51 g) obtained in (1) above, methyl trans-4-aminocyclohexane-carboxylate hydrochloride (5.27 g) obtained in Reference Example 2(1) and 1-hydroxybenzotriazole (5.06 g) are dissolved in N,N-dimethylformamide (100 ml). To the mixture are added 1-ethyl-3-(3-dimethylaminopropyl)-carbodiimide hydrochloride (7.10 g) and triethylamine (4.50 ml) successively under ice-cooling, and the mixture is stirred at room temperature for 3 days. The reaction solution is concentrated under reduced pressure, and to the resulting residue is added an aqueous sodium hydrogen carbonate solution, followed by extraction with ethyl acetate. The organic layer is washed with saturated brine, dried over sodium sulfate and evaporated to remove the solvent under reduced pressure. The resulting residue is purified by silica gel column chromatography (eluent: hexane/ethyl acetate=1:1 followed by ethyl acetate) to give methyl trans-4-({[2-(2-benzyloxy)ethoxy]acetyl}amino)-cyclohexanecarboxylate (8.24 g). APCI-MS M/Z:350[M+H]+

(3) Methyl trans-4-({[2-(2-benzyloxy)ethoxy]acetyl}-amino)cyclohexanecarboxylate (5.09 g) obtained in (2) above is dissolved in acetic acid (150 ml), and thereto is added 5% palladium carbon (1.01 g) and the mixture is stirred at room temperature for 2.4 hours under hydrogen atmosphere under normal pressure. The reaction solution is filtered to remove the catalyst, and the filtrate is concentrated under reduced pressure. The resulting residue is dissolved in chloroform, washed with saturated aqueous sodium hydrogen carbonate solution, dried over sodium sulfate and evaporated to remove the solvent to give methyl trans-4-{[(2-hydroxyethoxy)acetyl]amino}cyclohexanecarboxylate (3.32 g). APCI-MS M/Z:260[M+H]$^+$ (4) Methyl trans-4-{[(2-hydroxyethoxy)acetyl]amino}-cyclohexanecarboxylate (1.37 g) obtained in (3) above is dissolved in chloroform (15 ml), and thereto is added triethylamine (890 μl) under ice-cooling. Methanesulfonyl chloride (450 μl) is then added dropwise at the same temperature. The reaction solution is stirred for 3 hours under ice-cooling, diluted with water and extracted with chloroform. The organic layer is washed with saturated brine, dried over sodium sulfate and evaporated to remove the solvent under reduced pressure to give methyl trans-4-[({2-methylsulfonyl)oxy]ethoxy}acetyl)amino]cyclohexane-carboxylate (1.83 g). APCI-MS M/Z:338[M+H]$^+$ (5) Methyl trans-4-[({2-[(methylsulfonyl)oxy]ethoxy}-acetyl)amino]cyclohexanecarboxylate (1.08 g) obtained in (4) above is dissolved in N,N-dimethylacetamide (15 ml), and thereto is added 60% sodium hydride in oil (135 mg) under ice-cooling and the mixture is stirred at room temperature for 16 hours. The reaction solution is concentrated under reduced pressure, and to the resulting residue are added water and an excess sodium chloride, followed by extraction with chloroform. The organic layer is dried over sodium sulfate and evaporated to remove the solvent under reduced pressure. The resulting residue is purified by silica gel column chromatography (eluent: hexane/ethyl acetate=1:1 followed by ethyl acetate) to give methyl trans-4-(3-oxomorpholin-4-yl)cyclohexane-carboxylate (715 mg). APCI-MS M/Z:242[M+H]$^+$ (6) Methyl trans-4-(3-oxomorpholin-4-yl)cyclohexane-carboxylate (500 mg) obtained in (5) above is treated in a similar manner to Reference Example 2(4) to give the title compound (322 mg). ESI-MS M/Z:226[M−H]$^−$ Reference Example 5

Trans-4-(2-oxo-1,3-oxazolidin-3-yl)cyclohexanecar-boxylic acid

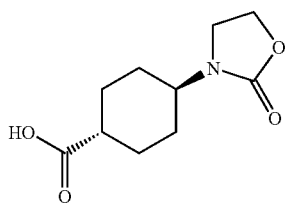

(1) Methyl trans-4-aminocyclohexanecarboxylate hydrochloride (5.00 g) obtained in Reference Example 2(1) is dissolved in chloroform (60 ml), and thereto is added triethylamine (11 ml) under ice-cooling, followed by dropwise addition of a solution of 2-chloroethyl chloroformate (3.3 ml) in chloroform (10 ml). After stirring at room temperature for 2.5 hours, to the reaction solution is added 5% hydrochloric acid and the mixture is extracted with chloroform. The organic layer is washed with saturated brine, dried over sodium sulfate, and then evaporated to remove the solvent under reduced pressure. The resulting residue is suspended in chloroform/diisopropyl ether. The precipitates are collected by filtration and dried to give methyl trans-4-{[(2-chloroethoxy)carbonyl]amino}cyclohexanecarboxylate (5.11 g). APCI-MS M/Z: 264/266[M+H]$^+$ (2) Methyl trans-4-{[(2-chloroethoxy)carbonyl]amino}-cyclohexanecarboxylate (3.70 g) obtained in (1) above is dissolved in N,N-dimethylacetamide (50 ml), and thereto is added 60% sodium hydride in oil (630 mg) under ice-cooling. The mixture is then stirred at room temperature for 16.5 hours. To the reaction solution is added water, and the mixture is extracted with ethyl acetate. The organic layer is washed with water and saturated brine, and then dried over sodium sulfate. The solvent is removed by evaporation under reduced pressure and the resulting residue is purified by silica gel column chromatography (eluent: hexane/ethyl acetate=1/1, followed by ethyl acetate) to give methyl trans-4-(2-oxo-1,3-oxazolidin-3-yl)cyclohexane-carboxylate (1.83 g). APCI-MS M/Z:228[M+H]$^+$ (3) Methyl trans-4-(2-oxo-1,3-oxazolidin-3-yl)-cyclohexanecarboxylate (1.84 g) obtained in (2) above is treated in a similar manner to Reference Example 2(4) to give the title compound (1.75 g). ESI-MS M/Z:212[M−H]$^−$ Reference Example 6

5-(2-oxopyrrolidin-1-yl)pentanoic acid

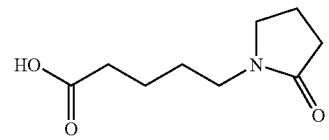

(1) 5-Aminovaleric acid (7.35 g) is dissolved in methanol (50 ml), and thereto is added dropwise thionyl chloride (4.9 ml) under ice-cooling. The reaction solution is then warmed to room temperature and stirred for 17 hours. The reaction solution is concentrated under reduced pressure. The resulting residue is suspended in diethyl ether and the precipitates are collected by filtration to give methyl 5-aminovalerate hydrochloride (9.93 g).
APCI-MS M/Z:132[M+H]$^+$ (2) Methyl 5-aminovalerate hydrochloride (1.68 g) obtained in (1) above is suspended in chloroform (20 ml), and to the suspension is added triethylamine (2.54 g) under ice-cooling, followed by dropwise addition of 4-chlorobutyryl chloride (1.55 g). The reaction solution is warmed to room temperature and stirred for 2 hours. Ice-water is poured to the reaction solution and the mixture is extracted with chloroform. The organic layer is washed with 10% hydrochloric acid, a saturated aqueous sodium hydrogen carbonate solution and saturated brine, and then dried over sodium sulfate. The solvent is evaporated under reduced pressure to give methyl 5-[(4-chlorobutanoyl)amino]pentanoate (2.34 g).
APCI-MS M/Z:236/238[M+H]$^+$ (3) Methyl 5-[(4-chlorobutanoyl)amino]pentanoate (2.33 g) obtained in (2) above is dissolved in N,N-dimethylacetamide (20 ml), and thereto is added 60% sodium hydride in oil (0.47 g) in small portions under ice-cooling. The reaction solution is warmed to room temperature, stirred for 20 hours and evaporated to remove the solvent under reduced pressure. The resulting residue is purified by silica gel column chromatography (eluent: chloroform followed by chloroform/ethyl acetate=20/1) to give methyl 5-(2-oxopyrrolidin-1-yl)pentanoate (2.15 g).

APCI-MS M/Z:200[M+H]$^+$ (4) Methyl 5-(2-oxopyrrolidin-1-yl)pentanoate (1.00 g) obtained in (3) above is dissolved in methanol (20 ml), and thereto is added 4 N aqueous sodium hydroxide solution (2.5 ml). The reaction solution is warmed to room temperature and stirred for 18 hours. The reaction solution is washed with diethyl ether, and thereto is added 2 N hydrochloric acid (5.0 ml), followed by concentration under reduced pressure. The resulting residue is extracted with chloroform and dried over sodium sulfate. The solvent is evaporated under reduced pressure to give the title compound (0.90 g). ESI-MS M/Z:184 [M–H]$^-$ Reference Example 7

5-(3-Oxomorpholin-4-yl)pentanoic acid

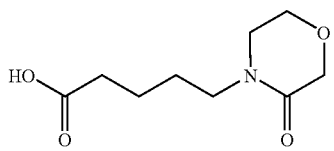

(1) Methyl 5-aminovalerate hydrochloride (3.35 g) obtained in Reference Example 6(1), [2-(benzyloxy)ethoxy]acetic acid (4.63 g) obtained in Reference Example 4(1) and 1-hydroxybenzotriazole (3.78 g) are dissolved in N,N-dimethylformamide (80 ml). To the mixture are added 1-ethyl-3-(3-dimethylaminopropyl)carbodiimide hydrochloride (5.37 g) and triethylamine (3.35 ml) successively under ice-cooling, and the mixture is stirred at room temperature for 2 days. The reaction solution is concentrated under reduced pressure, and the resulting residue is diluted with ice-water and extracted with ethyl acetate. The organic layer is washed with aqueous sodium hydrogen carbonate solution, water and saturated brine successively, dried over sodium sulfate and evaporated to remove the solvent under reduced pressure. The resulting residue is purified by silica gel column chromatography (eluent: hexane/ethyl acetate=1:1 followed by ethyl acetate) to give methyl 5-({[2-(benzyloxy)ethoxy]acetyl}amino)pentanoate (5.56 g).

APCI-MS M/Z:324[M+H]$^+$ (2) Methyl 5-({[2-(benzyloxy)ethoxy]acetyl}amino)-pentanoate (5.54 g) obtained in (1) above is dissolved in tetrahydrofuran (60 ml), and thereto is added 20% palladium hydroxide on carbon (0.5 g). The mixture is then stirred for 4 hours at room temperature under hydrogen atmosphere under normal pressure. The reaction solution is filtered to remove the catalyst, and then the filtrate is concentrated under reduced pressure to give methyl 5-{[(2-hydroxyethoxy)acetyl]amino}pentanoate (3.76 g). APCI-MS M/Z: 234[M+H]$^+$ (3) Methyl 5-{[(2-hydroxyethoxy)acetyl]amino}-pentanoate (1.17 g) obtained in (2) above is dissolved in chloroform (15 ml), and thereto is added triethylamine (0.84 ml) under ice-cooling. Methanesulfonyl chloride (0.43 ml) is then added dropwise to the mixture at the same temperature. The reaction solution is warmed to room temperature, stirred for 1 hour, and ice-water is poured thereto followed by extraction with chloroform. The organic layer is washed with saturated brine, dried over sodium sulfate and evaporated to remove the solvent under reduced pressure to give methyl 5-[({2-[(methylsulfonyl)oxy]ethoxy}acetyl)amino] pentanoate (1.51 g). APCI-MS M/Z:312[M+H]$^+$ (4) Methyl 5-[({2-[(methylsulfonyl)oxy]ethoxy}-acetyl)amino]pentanoate (1.48 g) obtained in (3) above is dissolved in N,N-dimethylacetamide (22 ml), and thereto is added 60% sodium hydride in oil (0.20 g) under ice-cooling. The mixture is then stirred at room temperature for 18 hours. Ice-water is poured to the reaction solution and the mixture is extracted with chloroform. The organic layer is washed with saturated brine, dried over sodium sulfate and the solvent is removed by evaporation under reduced pressure. The resulting residue is purified by silica gel column chromatography (eluent: hexane/ethyl acetate=1/1, followed by ethyl acetate) to give methyl 5-(3-oxomorpholin-4-yl)pentanoate (0.93 g).

APCI-MS M/Z:216[M+H]$^+$ (5) Methyl 5-(3-oxomorpholin-4-yl)pentanoate (500 mg) obtained in (4) above is dissolved in methanol (10 ml), and thereto is added an aqueous sodium hydroxide (0.40 g) solution (2 ml). The reaction solution is then warmed to room temperature and stirred for 17 hours. The reaction solution is concentrated under reduced pressure, neutralized with 2 N hydrochloric acid, and concentrated under reduced pressure. The resulting residue is extracted with chloroform, dried over sodium sulfate and evaporated to remove solvent under reduced pressure to give the title compound (0.35 g). ESI-MS M/Z: 200[M–H]$^-$ Reference Example 8

Trans-4-[(dimethylamino)carbonyl]-cyclohexanecarboxylic acid

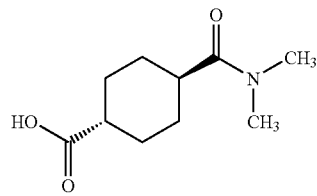

(1) Trans-4-(methoxycarbonyl)cyclohexanecarboxylic acid (20.0 g) obtained in Reference Example 1(2) is dissolved in chloroform (200 ml), and thereto are added dimethylamine hydrochloride (10.5 g), 1-ethyl-3-(3-dimethylaminopropyl)carbodiimide hydrochloride (24.7 g) and triethylamine (26.0 g) under ice-cooling. The mixture is then stirred at room temperature for 17 hours. Ice-water is poured to the reaction solution and the mixture is extracted with chloroform. The organic layer is washed with 10% hydrochloric acid, saturated aqueous sodium hydrogen carbonate solution and saturated brine successively and dried over sodium sulfate. The solvent is concentrated under reduced pressure and the resulting residue is purified by silica gel column chromatography (eluent: chloroform, followed by chloroform/methanol=20/1) to give methyl trans-4-[(dimethylamino)carbonyl]-cyclohexanecarboxylate (20.1 g). APCI-MS M/Z:214[M+H]$^+$ (2) Methyl trans-4-[(dimethylamino)carbonyl]cyclohexanecarboxylate (20.0 g) obtained in (1) above is dissolved in methanol (100 ml), and thereto is added a solution of sodium hydroxide (7.50 g) in water (40 ml). The mixture is then stirred at room temperature for 18 hours. The reaction solution is concentrated under reduced pressure, and the residue is diluted with ice-water and washed with diethyl ether. The resulting aqueous layer is acidified with 10% hydrochloric acid and extracted twice with chloroform. The organic layer is washed with saturated brine and dried over sodium sulfate. The solvent is concentrated under reduced pressure. The resulting residue is suspended in n-hexane and collected by filtration to give the title compound (15.7 g).

ESI-MS M/Z:198[M–H]$^-$

Reference Example 9

Trans-4-(pyrrolidin-1-ylcarbonyl)-cyclohexanecarboxylic acid

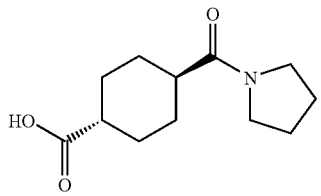

(1) Trans-4-(methoxycarbonyl)cyclohexanecarboxylic acid (20.0 g) obtained in Reference Example 1(2) is dissolved in chloroform (200 ml), and thereto are added pyrrolidine (9.2 g), 1-ethyl-3-(3-dimethyl-aminopropyl)carbodiimide hydrochloride (24.7 g) and triethylamine (13.6 g) under ice-cooling. The mixture is then stirred at room temperature for 17 hours. Ice-water is poured to the reaction solution and the mixture is extracted with chloroform. The organic layer is washed with 10% hydrochloric acid, saturated aqueous sodium hydrogen carbonate solution and saturated brine successively, and dried over sodium sulfate. The solvent is concentrated under reduced pressure. The resulting residue is purified by silica gel column chromatography (eluent: chloroform, followed by chloroform/methanol=20/1) to give methyl trans-4-(pyrrolidin-1-ylcarbonyl)-cyclohexanecarboxylate (11.8 g). APCI-MS M/Z: 240[M+H]$^+$ (2) Methyl trans-4-(pyrrolidin-1-ylcarbonyl)cyclo-hexanecarboxylate (11.7 g) obtained in (1) above is dissolved in methanol (50 ml), and thereto is added a solution of sodium hydroxide (3.95 g) in water (20 ml). The mixture is then stirred at room temperature for 18 hours. The reaction solution is concentrated under reduced pressure. The residue is diluted with ice-water and washed with diethyl ether. The resulting aqueous layer is acidified with 10% hydrochloric acid and extracted twice chloroform. The organic layer is washed with saturated brine and dried over sodium sulfate. The solvent is concentrated under reduced pressure. The resulting residue is suspended in n-hexane and collected by filtration to give the title compound (10.1 g).

ESI-MS M/Z:224[M–H]$^-$

Reference Example 10

Trans-4-(morpholin-4-ylcarbonyl)-cyclohexanecarboxylic acid

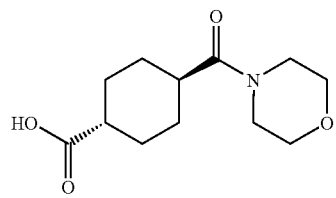

(1) Trans-4-(methoxycarbonyl)cyclohexanecarboxylic acid (800 mg) obtained in Reference Example 1(2) is dissolved in chloroform (30 ml), and thereto are added morpholine (560 mg), 1-ethyl-3-(3-dimethylaminopropyl)-carbodiimide hydrochloride (1.24 g) and triethylamine (650 mg) under ice-cooling. The mixture is then stirred at room temperature for 19 hours. Ice-water is poured to the reaction solution and the mixture is extracted with chloroform. The organic layer is washed with 10% hydrochloric acid, saturated aqueous sodium hydrogen carbonate solution and saturated brine successively and dried over sodium sulfate. The solvent is concentrated under reduced pressure. The resulting residue is purified by silica gel column chromatography (eluent: chloroform, followed by chloroform/methanol=30/1) to give methyl trans-4-(morpholin-4-ylcarbonyl)cyclohexanecarboxylate (897 mg). APCI-MS M/Z: 256[M+H]$^+$ (2) Methyl trans-4-(morpholin-4-ylcarbonyl)-cyclohexanecarboxylate (860 mg) obtained in Reference (1) above is dissolved in methanol (40 ml), and thereto is added 4 N aqueous sodium hydroxide solution (1.68 ml). The mixture is then stirred at room temperature for 18 hours. The reaction solution is concentrated under reduced pressure. The residue is diluted with ice-water, neutralized with 10% hydrochloric acid and extracted with chloroform. The organic layer is dried over sodium sulfate and the solvent is concentrated under reduced pressure to give title compound (638 mg). ESI-MS M/Z:240[M–H]$^-$

Reference Example 11

Trans-4-{[[2-(dimethylamino)ethyl]-(methyl)amino]carbonyl}cyclohexanecarboxylic acid

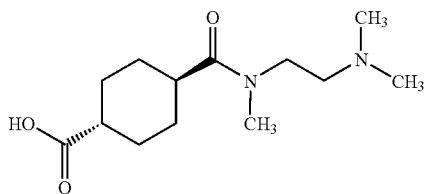

(1) Trans-4-(methoxycarbonyl)cyclohexanecarboxylic acid (8.84 g) obtained in Reference Example 1(2) is dissolved in chloroform (100 ml), and thereto are added 1-hydroxybenzotriazole (7.14 g), 1-ethyl-3-(3-dimethyl-aminopropyl)carbodiimide hydrochloride (10.00 g) and N,N,N'-trimethylethylenediamine (5.33 g) under ice-cooling. The mixture is then stirred at room temperature for 4 hours. Saturated aqueous sodium hydrogen carbonate solution is poured to the reaction solution and the mixture is extracted with chloroform. The organic layer is washed with saturated brine and dried over sodium sulfate. The solvent is concentrated under reduced pressure. The resulting residue is purified by silica gel column chromatography (eluent: chloroform/methanol/28% ammonia water=200/10/1) to give methyl trans-4-{[[2-(dimethylamino)ethyl](methyl)amino]carbonyl}cyclohexane-carboxylate (11.98 g). APCI-MS M/Z:271[M+H]$^+$ (2) Methyl trans-4-{[[2-(dimethylamino)ethyl]-(methyl)amino]carbonyl}cyclohexanecarboxylate (6.32 g) obtained in (1) above is dissolved in methanol (20 ml), and thereto is added 1 N aqueous sodium hydroxide solution (25 ml). The mixture is stirred at room temperature for 3 hours. To the reaction solution is added 1 N hydrochloric acid (25 ml) and the reaction solution is concentrated under reduced pressure. The residue is lyophilized to give the crude title compound which contains equimolar sodium chloride (6.71 g). APCI-MS M/Z:257[M+H]$^+$

INDUSTRIAL APPLICABILITY

The compound of the formula (I) or a pharmaceutically acceptable salt thereof is less toxic and safe, and has an excellent inhibitory effect on FXa. Accordingly, the said compound (I) is useful as a medicament for prevention and treatment of diseases caused by thrombi or emboli.

What is claimed is:

1. An amide-type carboxamide derivative of the formula [1]:

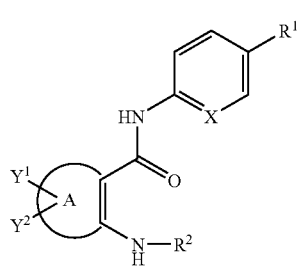

wherein X is a group of the formula: —N= or the formula: —CH=;

$Y^1$ and $Y^2$ are the same or different and each is a group selected from a hydrogen atom, a halogen atom, a lower alkyl group, a lower alkoxy group, a lower alkyl group substituted by halogen atom, a lower alkoxycarbonyl group, a carboxyl group, a lower alkylcarbamoyl group and a phenyl group;

$R^1$ is a hydrogen atom, a halogen atom, a lower alkyl group or a lower alkoxy group;

$R^2$ is a group of the formula: —CO—$R^{21}$—$R^{22}$;

$R^{21}$ is a lower alkylene group or a cycloalkanediyl group; and $R^{22}$ is a group of the formula:

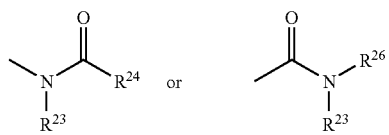

wherein $R^{23}$ and $R^{24}$ are the same or different and each is a lower alkyl group or an amino-lower alkyl group optionally substituted by a lower alkyl group; or combine together at the ends to form an optionally substituted nitrogen-containing saturated heterocyclic group along with the adjacent group: —N—C(=O)—; $R^{25}$ and $R^{26}$ are the same or different and each is a lower alkyl group or an amino-lower alkyl group optionally substituted by a lower alkyl group; or combine together at the ends to form an optionally substituted nitrogen-containing saturated heterocyclic group along with the adjacent nitrogen atom; and Ring A is an aromatic hydrocarbon, a monocyclic heteroaromatic ring or a condensed thiophene ring, or a pharmaceutically acceptable salt thereof.

2. The compound according to claim 1, wherein Ring A is benzene, naphthalene, pyridine, furan, thiophene, pyrazole, benzothiophene or thienopyridine.

3. The compound according to claim 2, wherein $R^2$ is

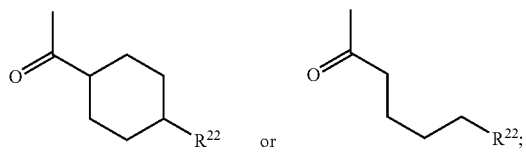

$R^{22}$ is a group of the formula:

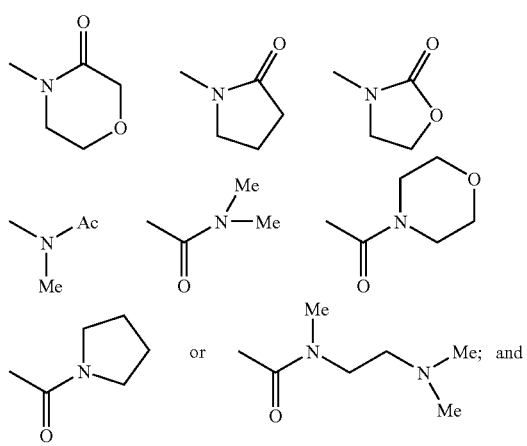

-continued

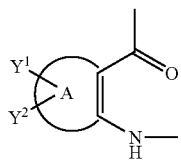

is a group of the formula:

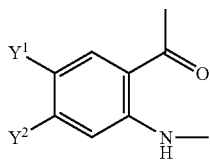 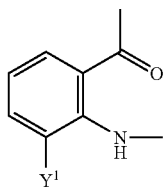

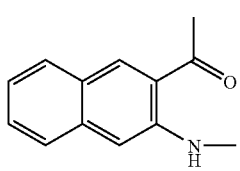 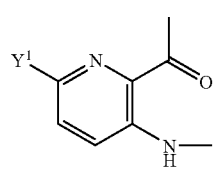

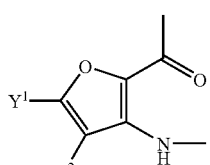 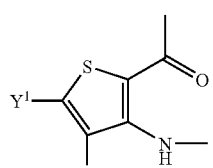

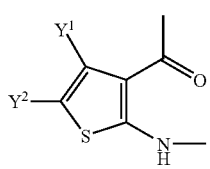 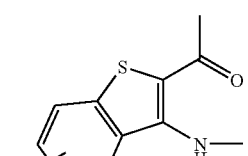

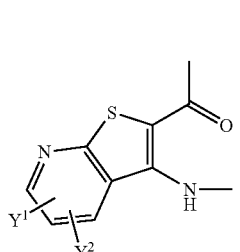 or 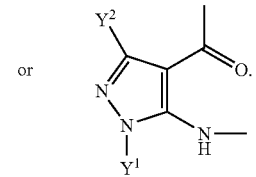

4. The compound according to claim 2, wherein $R^1$ is a halogen atom or a lower alkyl group;

$R^2$ is a group of the formula:

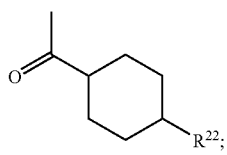

$R^{22}$ is a group of the formula:

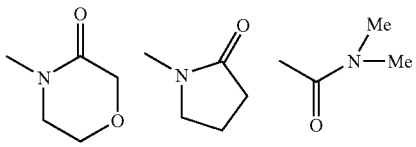

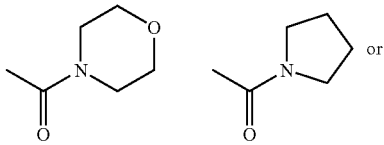

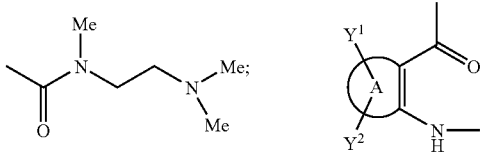

is a group of the formula:

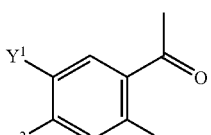 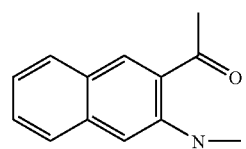

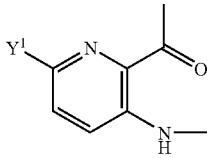 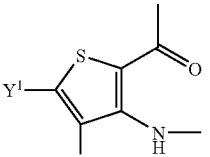

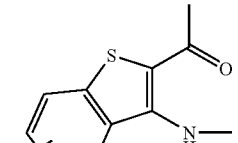 or

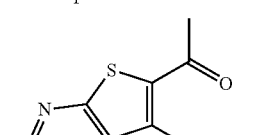

and $Y^1$ and $Y^2$ are the same or different and each is a group selected from a hydrogen atom, a halogen atom, a lower alkyl group, a lower alkoxy group and a carboxyl group.

5. The compound according to claim 4, wherein

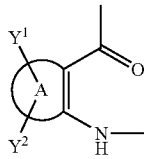

is a group of the formula:

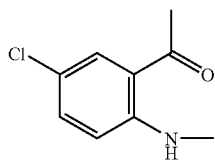 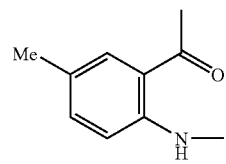

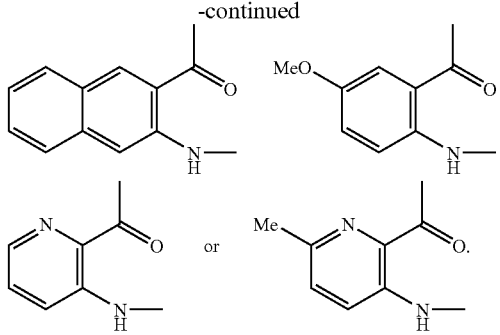

6. A pharmaceutical composition, which comprises as an active ingredient a compound according to any one of claims 1 to 5, or a pharmaceutically acceptable salt thereof.

7. A method for treatment of thrombosis, which comprises administering an effective amount of a compound according to any one of claims 1 to 5, or a pharmaceutically acceptable salt thereof, to a patient in need thereof.

* * * * *